US00RE38793E

(19) United States
(12) Reissued Patent
Rinehart et al.

(10) Patent Number: US RE38,793 E
(45) Date of Reissued Patent: Sep. 6, 2005

(54) SPISULOSINE COMPOUNDS

(76) Inventors: Kenneth L. Rinehart, 1306 S. Carle Ave., Urbana, IL (US) 61801; Nancy L. Gallagher, 208 Crabtree La., Vernon Hills, IL (US) 60061; Robert A. Warwick, 605 W. Iowa St., Urbana, IL (US) 61801

(21) Appl. No.: 10/219,050

(22) Filed: Aug. 14, 2002

Related U.S. Patent Documents

Reissue of:
(64) Patent No.: 6,107,520
Issued: Aug. 22, 2000
Appl. No.: 09/058,456
Filed: Apr. 10, 1998

U.S. Applications:
(60) Provisional application No. 60/043,326, filed on Apr. 15, 1997, and provisional application No. 60/043,599, filed on Apr. 15, 1997.

(51) Int. Cl.[7] ..... C07C 213/00; C07C 215/00; C07C 217/00
(52) U.S. Cl. ..... 564/360; 514/459
(58) Field of Search ..... 564/360; 514/459, 514/360

(56) References Cited

U.S. PATENT DOCUMENTS

| | | | | |
|---|---|---|---|---|
| 4,816,450 A | | 3/1989 | Bell et al. | 514/25 |
| 5,190,876 A | | 3/1993 | Merrill, Jr. et al. | 435/240 |
| 5,426,228 A | * | 6/1995 | Koskinen et al. | 564/360 |

FOREIGN PATENT DOCUMENTS

| | | | |
|---|---|---|---|
| EP | 0 381 514 A2 | 8/1990 | A61K/31/13 |
| EP | 0 821 068 A2 | 1/1998 | C12P/13/02 |
| WO | WO 96/18404 | 6/1996 | A61K/31/70 |

OTHER PUBLICATIONS

Nancy Louise Fregeau, Ph.D. Thesis entitled "Biologically Active Compounds from a Claim and a Tunicate" submitted in partial fulfillment of the requirements for the degree of Doctor of Philosophy in chemistry in the Graduate College of the University of Illinois at Urbana–Champaign, 1992. First released to the public by the University—Apr. 14, 1998.

Barry C. Smith et al., "Phytoplankton Pigments Accumulated by the Arctic Surfclam," Journal of Shellfish Research, vol. 11, No. 2, pp. 479–483, 1992.

R.S. Shallenberger et al., Laminaranase Activity in the Crystalline Style of the Surf Clam, Experientia, vol. 30, pp. 597–598, 1974.

H. Sun et al., "Weinbersterol Disulfates A and B, Antiviral Steriod Sulfates from the Sponge *Petrosia Weinbergi", Tetrahedron,* vol. 47, No. 7, pp. 1185–1190 (1991).

S. Sakemi et al., "Antitumor Cyclic Peroxides from the Sponge *Plakortis Lita", Tetrahedron,* vol. 43, No. 1, pp. 263–268 (1987).

S. Sakemi et al., "Isolation and Structure Elucidation of Onnamide A. a New Bioactive Metabolite of a Marine Sponge, *Theonella* sp.", *J. Am. Chem. Soc.,* vol. 110, pp. 4851–4853 (1988).

(Continued)

*Primary Examiner*—James O. Wilson
*Assistant Examiner*—Everett White
(74) *Attorney, Agent, or Firm*—Kenneth H. Sonnenfeld; Michael A. Willis; Morgan & Finnegan, L.L.P.

(57) ABSTRACT

The present invention is directed to the isolation and bioactive characterization of compounds isolated from the clam Spisula polynyma. These compounds include three sphingoid-type bases, spisulosines 285, 299 and 313 (1–3), each of which shows unique cytotoxicity against L1210 murine lymphocytic leukemia cells. In addition, sphingosine (also referred to as 4-sphingenine or octadeca-4-shpingenine, 4) and two related compounds, nonadeca-4-sphingenine (a one carbon longer homolog, 5) and sphinga-4,10-diene (a dehydrosphingosine deravitive, 6) were also obtained, These compounds also contribute to the cytotoxicity of the Spisula polynyma extracts, but did not cause the morphology changes observed with compounds 1–3.

8 Claims, 2 Drawing Sheets

OTHER PUBLICATIONS

M. Murata et al., "Structures and Configurations of Ciguatoxin from the Moray Eel *Gymnothorax javanicus* and Its Likely Precursor from the Dinoflagellate *Gambierdiscus toxicus", J. Am. Chem. Soc.,* vol. 112, pp. 4380–4386 (1990).

M. Kernan et al., "Macrocyclic Antifungal Metabolites from the Spanish Dancer Nudibranch *Hexabranchus sanguineus* andd Sponges of the Genus *Halichondria", J. Org. Chem.,* vol. 53, pp. 5014–5020 (1988).

G. Pettit et al., "Antneoplastic Agents. 224 Isolation and Structure of Neristatin 1[1a]", *J. Am. Chem. Soc.,* vol. 113, No. 17, pp. 6693–6695 (1991).

D. Schaufelberger et al., "Revised Structure of Byrostatin 3 and Isolation of the Bryostatin 3 26–Ketone from *Bugula neritina", J. Org. Chem.,* vol. 56, pp. 2895–2900 (1991).

W. Murayama et al., "A New Centrifugal Counter–Current Chromatograph and Its Application", *Journal of Chromatography,* vol. 239, pp. 643–649 (1982).

D. Martin et al., "Countercurrent Chromatography for Drug Discovery and Development", *CCC for Drug Discovery and Development,* Chapter Nine, pp. 565–581.

S. Kohmoto et al., "Isospongiadiol, a Cytotoxic and Antiviral Diterpene from a Caribbean Deep Water Marine Sponge, *Spongia* sp.", *Chemistry Letter,* pp. 1687–1690 (1987).

G. Pettit et al., "Isolation and Structure of Bryostatins 14 and 15[1]", *Tetrahedron,* vol. 47, No. 22, pp. 3601–3610 (1991).

R. Bruening et al., "Isolation of Tunichrome B–1, A Reducing Blood Pigment of the Sea Squirt, *Ascidia Nigra*[1]", *Journal of Natural Products,* vol. 49, No. 2, pp. 193–204 (1986).

M. Reetz et al., "Sterioselective Synthesis of β–Amino Alcohols from Optically Active a–Amino Acids", *Angew. Chem. Int. Ed. Eng.,* vol. 26, No. 11, pp. 1141–1143 (1987).

Prostenik et al., "Application of the Asymmetric Synthesis in the Determination of the Configuration of Amino Alcohols and Diamines with Two Adjacent Asymmetric Carbon Atoms", *Croatica Chemica Acta,* vol. 29, pp. 393–402 (1957).

B. Ravi et al., "Recent Research in Marine Natural Products: The Puupehenones", *Pure & Appl. Chem.,* vol. 51, pp. 1893–1900, (1979).

A. Stierle et al., "A Marine *Micrococcus* Produces Metabolites Ascribed to the Sponge *Tedania ignis", Experientia,* vol. 44, pp. 1021 (1988).

F. Schmitz et al., "Metabolites from the Marine Sponge *Tedania ignis.* A New Atisanediol and Several Known Diketopiperazines[1]", *J. Org. Chem.,* vol. 48, pp. 3941–3945 (1983).

R. Dillman et al., "An Unusual Sulfur–Containing Diketopiperazine from the Bermudian Sponge *Tedania Ignis*[1]", *Journal of Natural Products,* vol. 54, No. 4, pp. 1159–1161 (1991).

A. Stierle et al., "Maculosin, a host–speciific phytotoxin for spotted knapweed from *Alternaria alternata", Proc. Natl. Acad. Sci USA,* vol. 85, pp. 8008–8011 (1988).

A. Stierle et al., "Benzothiazoles From a Putative Bacterial Symbiont of the Marine Sponge *Tedania ignis*[1]", *Tetrahedron Letters,* vol. 32, No. 37, pp. 4847–4848 (1991).

M. Raub et al., "Clavepictines A and B: Cytotoxic Quinolizines From the Tunicate *Clavelina picta*[1]", *J. Am. Chem. Soc.,* vol. 113, pp. 3178–3180 (1991).

S. Sakemi et al., "Xestamines A, B and C, Three New Long–Chain Methoxylamine Pyridines from the Sponge *Xestopongia Weidenmayeri", Journal of Natural Products,* vol. 53, No. 4, pp. 995–999 (1990).

D. Steirle et al., "Antimicrobial N–Methylpyridinium Salts Related to the Xestamines From the Caribbean Sponge *Calyx Podatypa", Journal of Natural Products,* vol. 54, No. 4, pp. 1134–1136 (1991).

S. Kohmoto et al., "1,1–Dimethyl–5–6– dihydroxyindolinium chloride from a deep water marine spong, *Dercitus* sp.", *Experientia,* vol. 44, pp. 85–86, (1988).

H. Sun, et al., "A Brominated (Aminoimidazolinyl)indole from the Sponge *Discodermia polydiscus", J. Org. Chem.,* vol. 56, pp. 4307–4308 (1991).

R. Sakai et al., "Manzamine B and C, Two Novel Alkaloids from the Sponge *Halicloma* sp.", *Tetrahedron Letters,* vol. 28, No. 45, pp. 5493–5496 (1987).

S. Bobzin et al., Aromatic Alkaloids from the Marine Sponge *Chelonaplysilla* sp., *J. Org. Chem.,* vol. 56, pp. 4403–4407 (1991).

S. Sakemi et al., "Nortopsentins A, B, and C. Cytotoxic and Antifungal Imidazolediylbis[indoles] from the Sponge *Spongosorites ruetzleri", J. Org. Chem.,* vol. 56, pp. 4304–4307 (1991).

P. Keifer et al., "Bioactive Bromopyrrole Metabolites from the Caribbean Sponge *Angelas conifera", J. Org. Chem.,* vol. 56, pp. 2965–2975 (1991).

F. Schmitz et al., "Biologically active compounds from marine organisms", *Pure & Appl. Chem.,* vol. 62, No. 7, pp. 1393–1396 (1990).

D. Schaufelberger et al., "Separation of Pyrroloimidazoles from Indo–Pacific Marine Sponges by High–Speed Countercurrent Distribution", *Journal of Liquid Chromatography,* pp. 1909–1917 (1989).

G. Pettit et al., "Antineoplastic agents. 168. Isolation and structure of axinonydantoin[1]", *Can. J. Chem.,* vol. 68, pp. 1621–1624 (1990).

F. Schmitz et al., "Cytotoxic Aromatic Alkaloids from the Ascidian *Amphicarpa meridiana* and *Leptoclinides* sp.: Meridine and 11–Hydroxyascididemin", *J. Org. Chem.,* vol. 56, pp. 804–808 (1991).

G. Gunawardana et al., "Dercitin, a New Biologically Active Acridine Alkaloid from a Deep Water Marine Sponge, *Dercitus* sp.", *J. Am. Chem. Soc.,* vol. 110, pp. 4856–4848 (1988).

G. Gunawardana et al., "Pyridoacridine Alkaloids from Deep–Water Marine Sponges of the Family Pachastrellidae: Structure Revision of Dercitin and Related Compounds and Correlation with the Kuanoniamines", *J. Org. Chem.,* vol. 57, pp. 1523–1526 (1992).

G. Gunawardana et al., "New Cytotoxic Acridine Alkaloids from Two Deep Water Marine Sponges of the Family Pachastrellidae", *Tetrahedron Letters,* vol. 30, No. 33, pp. 433359–4362 (1989).

S. Sakemi et al., "Batzellines A, B, C, Novel Pyrroloquinoline Alkaloids From the Sponge *Batzella* Sp.", *Tetrahedron Letters,* vol. 30, No. 19, pp. 2517–2520 (1989).

H. Sun et al., "Isobatzellines A, B, C, and D. Cytotoxic and Antifungal Pyrroloquinoline Alkaloids from the Marine Sponge *Batzella* sp.", *J. Org. Chem.,* vol. 55, pp. 4964–4966 (1990).

G. Kalaus et al., "Synthesis of Vinca Alkaloids and Related Compounds. 37[1]. Some New Reactions of (±)–C–Norquebrachamine and Its Derivatives", *J. ORg. Chem.,* vol. 53, pp. 42–45 (1988).

E. Jares–Erijman et al., "Crambescidins: New Antiviral and Cytotoxic Compounds from the Sponge *Crambe crambe*[1]", *J. Org. Chem.,* vol. 56, pp. 5712–5715 (1991).

Y. Kashman, et al., "Ptilomycalin A: A Novel Polycyclic Guanidine Alkaloid of Marine Origin", *J. Am. Chem. Soc.,* vol. 111, pp. 8925–8926 (1989).

R. Berlinck et al., "Two new guanidine alkaloids from the Mediterranean sponge *Crambe crambe", Tetrahedron Letter,* vol. 31, No. 45, pp. 6531–6534 (1990).

K. Rinehart et al., "Ecteinascidins 729, 743, 745, 759A, 759B, and 770: Potent Antitumor Agents from the Caribbean Tunicate *Ecteinascidia turbinata*[1]", *J. Org. Chem.,* vol. 55, pp. 4512–4515 (1990).

A. Wright, et al., "Antitumor Tetrahydroisoquinolline Alkaloids from the Colonial Ascidian *Ecteinascidia turbinata", J. Org. Chem.,* vol. 55, pp. 4508–4512 (1990).

R. Brusca and G. Brusca, *Invertebrates,* Sinauer Associates, Sunderland, MA, (1990), pp. 706–709.

B. Palameta et al., "Chromatography of the Lipide Bases on Paper Impregnated with Silicic Acid", *Croatica Chemica Acta,* vol. 33, pp. 133–135 (1961).

Y. Kawano et al., "Isolation and Structure of Six New Cerebrosides", *Biologically Active Glycosides from Asteroidea, XIII,* pp. 19–24, Liebigs Ann. Chem., 1988, pp. 19–24.

N. Gulavita et al., "Two Epimeric Aliphatic Amino Alcohols from a Sponge, *Xestopongia* sp.[1]", *J. Org. Chem.,* vol. 54, No. 2, pp. 367–369 (1989).

C. Jimenez et al., "Novel Marine Sponge Amino Acids, 10.[1] Xestoaminols from *Xestospongia* Sp.", *Journal of Natural Products,* vol. 53, No. 4, pp. 978–982 (1990).

K. Mori et al., "Synthesis and Absolute Configuration of the Two Epimeric Aliphatic Amino Alcoholss [(5E, 7E)–2–Amino–5,7–tetradecadien–3–ols] Isolated from a Sponge, *Xestrospongia* sp.", *Synthesis if Sphingosine Relative, XIII,* pp. 131–137. Liebigs Ann. Chem., 1992, pp. 131–137.

J. Osby et al., "An Exceptionally Mild Deprotection of Phthalimides", *Tetrahedron LettersI,* vol. 25, No. 20, pp. 2093–2096 (1984).

W. Stoffel, "Sphingolids" (1971), pp. 57–82.

A. Merrill et al., "Structural Requirement for Long–Chain (Sphingoid) Based Inhibition of Protein Kinase C in Vitro and for the Cellular Effects of These Compounds", *Biochemistry,* vol. 28, pp. 3138–3145 (1989).

Y. Hannun et al., "Functions of Sphingolipids and Sphingolipid Breakdown Products in Cellular Regulation", *Science,* vol. 243, pp. 500–507.

A. Merrill, "Cell Regulation by Sphingosine and More Complex Sphingolipids[1]", *Journal of Bioenergetics and Biomembranes,* vol. 23, No. 1, pp. 83–104 (1991).

J. Witten et al., "Structure of Two Cockroach Neuropeptides Assigned by Fast Atom Bombardment Mass Spectrometry", *Biochemical and Biophysical Research Communication,* vol. 124, No. 2, pp. 350–358 (1984).

E. Hermann et al., "The Detection, Assay and Evaluation of Antiviral Drugs", *Progr. med. Virol.,* vol. 3, pp. 158–192 (1961).

S. Grode et al., "Ceramides from the Sponge *Dysidea etheria*[1]", *Lipids,* vol. 18, No. 12, pp. 889–893 (1983).

*Chem. Abs.,* 1991, 114, 214413b.

D.J. Faulkner, "Marine Natural Products", *Nat. Prod. Rep.,* vol. 8, pp. 97–147 (1991).

M.H.G. Munro, et al., "The Search for Antiviral and Anticancer Compounds from Marine Organisms", *Bioorganic Marine Chemistry,* vol. 1, pp. 93–176 (1987).

* cited by examiner

1A

1D

1B

1E

1C

1F

SPISULOSINE COMPOUNDS

Matter enclosed in heavy brackets [ ] appears in the original patent but forms no part of this reissue specification; matter printed in italics indicates the additions made by reissue.

CROSS-REFERENCE TO RELATED APPLICATIONS

This application claims the benefit of U.S. Provisional Application Serial No. 60/043,326 filed Apr. 15, 1997, and U.S. Provisional Application Serial No. 60/043,599 filed Apr. 15, 1997, the teachings of which are incorporated herein by reference.

*This invention was made with Government support under Contract No. AI-04769 awarded by the National Institutes of Health (NIH). The Government has certain rights in the invention.*

BACKGROUND OF THE INVENTION

Rinehart et al. have long been interested in isolating bioactive compounds from marine organisms. To this end, we have established an in-house in vitro screening program to test crude extracts for antimicrobial, antiviral, and cytotoxic activities. Once an organism with interesting biological activity has been identified, we use these assays to guide our purification of the compounds responsible for the bioactivity.

Spisula polynyma is an edible clam, which is also known as the Stimpson surf clam or the Atlantic surf clam. It belongs to the subfamily Mactrinae, family Mactridae, superfamily Mactroidea, order Veneroida, subclass Heterodonta, class Bivalvia, phylum Mollusca. S. polynyma was originally found off the coast of Japan, where it is called hokkigai and processed for sushi. It has now migrated through the Bering Strait, down past Greenland and Newfoundland, into the Atlantic ocean. The clam has a grey-white shell, 7–10 cm long. It is mainly off-white, except for the tongue which is purple in the living clam, but turns bright red after cooking.

For this invention, S. polynyma were collected, at a depth of −110 feet, from a clam bed on the eastern edge of Stellwagon bank which is located off the coast of New England, stretching from near Gloucester, Mass., north to Maine. They were shipped to us live by the New England Clam Corporation (formerly New Dawn Seafoods, Inc.) and then immediately frozen.

To test for biological activity, one clam was homogenized in 3:1 methanol/toluene. A solution of sodium chloride was added to this crude extract, causing it to separate into a toluene and an aqueous layer. The latter was further extracted with toluene, dichloromethane, ethyl acetate and 1-butanol. These extracts were all assayed against L1210 cells, where significant cytotoxicity was observed for the initial crude, toluene and dichloromethane extracts and less activity in the other three fractions. See Table I.

TABLE I

L1210 Cytotoxicity of Crude Extracts of *S. polynyma*[a,b]

| Extract | Concentration (ug/mL) 250 | 125 | 50 | 25 | 12.5 | 5 |
|---|---|---|---|---|---|---|
| Crude | 98* | 98* | 92 | 25 | 0 | 0 |
| Toluene | 100* | 100* | 100* | 25 | 13 | 13 |
| $CH_2Cl_2$ | 100* | 100* | 100* | 91 | 20 | 13 |
| EtOAc | 98* | 98* | 92* | 0 | 0 | 0 |
| 1-BuOH | 83 | 33 | 0 | 0 | 0 | 0 |
| aqueous[c] | 94 | 75 | 0 | 0 | 0 | 0 |

Footnotes:
[a]cytoxicity reported as % inhibition of growth;
[b]entries marked with * showed pointed cell activity;
[c]the aqueous extract was assayed at 700, 350, 140 70, 35 and 14 ug/mL.

These extracts were also assayed against Herpes simplex virus Type I (HSV-1) and CV-1 monkey kidney cells (at 100 μug/6.35-mm disk), but no activity was observed. No antimicrobial activity was observed for these extract against Penicillium melinii (formerly P. atrovenetum) and Micrococcus luteus (formerly Sarcina lutea, both at 500 μg/12.7-mm-disk). Later, other more purified extracts were assayed against Bacillus subtilis, Saccharomyces cerevisiae, and Escherichia coli with no bioactivity observed.

SUMMARY OF THE INVENTION

The present invention is directed to the isolation and bioactive characterization of compounds isolated from the clam Spisula polynyma. These compounds include three sphingoid-type bases, spisulosines 285, 299 and 313 (1–3), each of which shows unique cytotoxicity against L1210 murine lymphocytic leukemia cells. In addition, sphingosine (also referred to as 4-sphingenine or octadeca-4-shpingenine, 4) and two related compounds, nonadeca-4-sphingenine (a one carbon longer homolog, 5) and sphinga-4,10-diene (a dehydrosphingosine deravitive, 6) were also obtained. These compounds also contribute to the cytotoxicity of the Spisula polynyma extracts, but did not cause the morphology changes observed with compounds 1–3.

The structures of the compounds isolated from extracts of the clam Spisula polynyma are as follows:

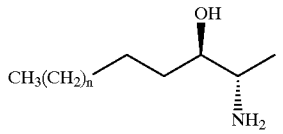

Spisulosine 285 (1), n=12; Spisulosine 299 (2), n=13; Spisulosine 313 (3), n=14; as well as:

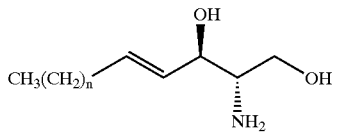

Sphingosine (4), n=12 and nonadeca-4-sphingenine (5), n=13; and

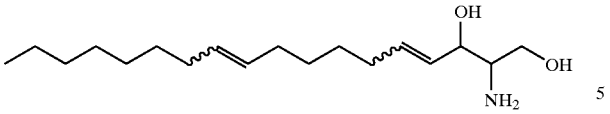

sphinga-4,10-diene (6).

Scheme 1

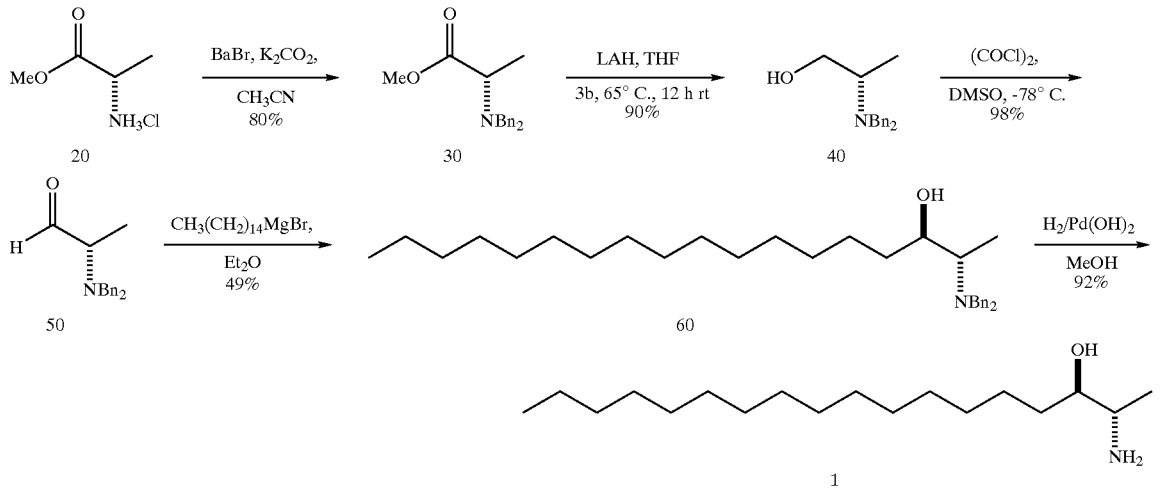

Compounds 1–3 show unique cytotoxicity against L1210 murine lymphocytic leukemia cells. In a number of the L1210 assays, a distinct morphological altercation was observed; some of the cells changed from being spherical (FIG. 1A) to ovoid with long points approximately 180° apart (FIG. 1B). Several other forms have also been observed in assays of these extracts, including cells with points not 180° apart (FIG. 1C), cells with more than two pints (FIG. 1D), cells with a bulge (FIG. 1E) and cells with a bulge replacing one of the points (FIG. 1F). However, the form with two sharp, opposing points was by far the predominant and characteristic one observed. This type of morphological change had not previously been observed during the screening of over 1000 marine extracts.

Thus, one embodiment of the present invention is directed to novel compounds isolated from the clam Spisula polynyma, and the use of all of the cytotoxic compounds isolated therefrom as antitumor compounds.

Another embodiment of the present invention is a synthetic method for the preparation of spisulosine 285 (1). Compound 1 and the syn diastereometer, were first synthesized by Croatian researchers in the determination of absolute configurations of lipid bases with two or more asymmetric carbon atoms. See, Prostenik, M., Alaupovic, P. Croat. Chem, Acta. 1957, 29,393.

The preferred synthetic route is based upon the previous addition of organometallics to N,N-dibenzylamino aldehydes to yield β-amino alcohols with high stereoselectivity. See, Andres et al., Org. Chem. 1996, 61, 4210 and Reetz et al., Angew Chem. Int. Ed. Engl., 1987, 26, 1141. The non-chelation controlled addition of Grignard reagents or organolithium compounds produces the anti-diastereomer and the chelation controlled addition of organozinc preferentially gives the syn-diastereomer.

Scheme I illustrates this preferred synthetic process for the formation of Compound 1:

As described in Scheme I, the α-amino aldehyde 50 was prepared from L-alanine methyl ester by first dibenzylation of the amino group with benzyl bromide and potassium carbonate followed by lithium aluminum hydride reduction to the N,N-dibenzylamino alcohol 40. The Swern oxidation of 40 gave 50 in high yield and was used without further purification to avoid decomposition. Addition of the Grignard reagent to 50 gave the anti-diastereomer 60 with high selectivity. The compound, 60, was easily purified by flash chromatography and HPLC. The deprotection of 60 by hydrogenolysis on Pearlman's catalyst gave 1 in 92% yield and a overall yield of 33%. Compounds 2 and 3 may be prepared simply by increasing the chain length of the Grignard reagent.

The assignment of the 2S,3R configuration is based on comparison of the chemical shifts of the benzyl protons in 60 to literature values for the syn and anti diastereomers of 2-(N,N-dibenzylamino)-3-pentanol. The anti isomer has a chemical shift difference of 0.29 ppm and the syn is 0.52 ppm. Comparison of other syn-anti pairs show the range for the syn isomer to be 0.44 to 0.54 ppm and the anti 0.05 to 0.29 ppm. The value for 60 is 0.29 ppm.

This synthetic sample of 1, was assayed against L1210 leukemia cells and showed both cytotoxicity and pointed cell activity (Table 1).

TABLE 1

L1210 Inhibition and pointed cell activity

| Concentration | % cytoxicity | % pointed cells[a] |
|---|---|---|
| 0.5 μg/mL | 100 | 97 |
| 0.25 μg/mL | 99 | 100 |
| 0.1 μg/mL | 99 | 62 |

TABLE 1-continued

| L1210 Inhibition and pointed cell activity | | |
|---|---|---|
| Concentration | % cytoxicity | % pointed cells[a] |
| 0.05 μg/mL | 96 | 71 |
| 0.025 μg/mL | 90 | 21 |
| 0.01 μg/mL | 45 | 1 |

[a]Percent pointed cells are a percent of the living cells.

Spisulosine 285 (1) is also active against other tumor cell lines in vitro, including P-388 (0.01 ug/ml); A-549 (0.05 ug/ml); HT-29 (0.05 ug/ml) and MEL-28 (0.05 ug/ml).

As shown above, the present invention is directed to bioactive compounds. These compounds have been prepared in substantially pure form, i.e., at a purity level sufficient to allow physical and biological characterization thereof. As described above, these compounds have been found to possess specific antitumor activities and as such they will be useful as medicinal agents in mammals, particularly in humans. Thus, another aspect of the present invention concerns pharmaceutical compositions containing the active compounds identified herein and methods of treatment employing such pharmaceutical compositions.

The active compounds of the present invention exhibit antitumor activity. Thus, the present invention also provides a method of treating any mammal affected by a malignant tumor sensitive to these compounds, which comprises administering to the affected individual a therapeutically effective amount of an active compound or mixture of compounds, or pharmaceutical compositions thereof. The present invention also relates to pharmaceutical preparations, which contain as active ingredient one or more of the compounds of this invention, as well as the processes for its preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

The correct dosage of a pharmaceutical composition comprising the compounds of this invention will vary according to the particular formulation, the mode of application, and the particular situs, host and bacteria or tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

BRIEF DESCRIPTION OF THE DRAWINGS

FIG. 1A represents a normal cell; FIG. 1B represents a typical pointed cell; FIG. 1C represents an atypical pointed cell; FIG. 1D represents a cell with more than two points; FIG. 1E represents a bulged cell; and FIG. 1F represents a combined bulged and pointed cell.

DETAILED DESCRIPTION OF THE INVENTION

Isolation of Spisulosines 285, 299, and 313

Figure 2:
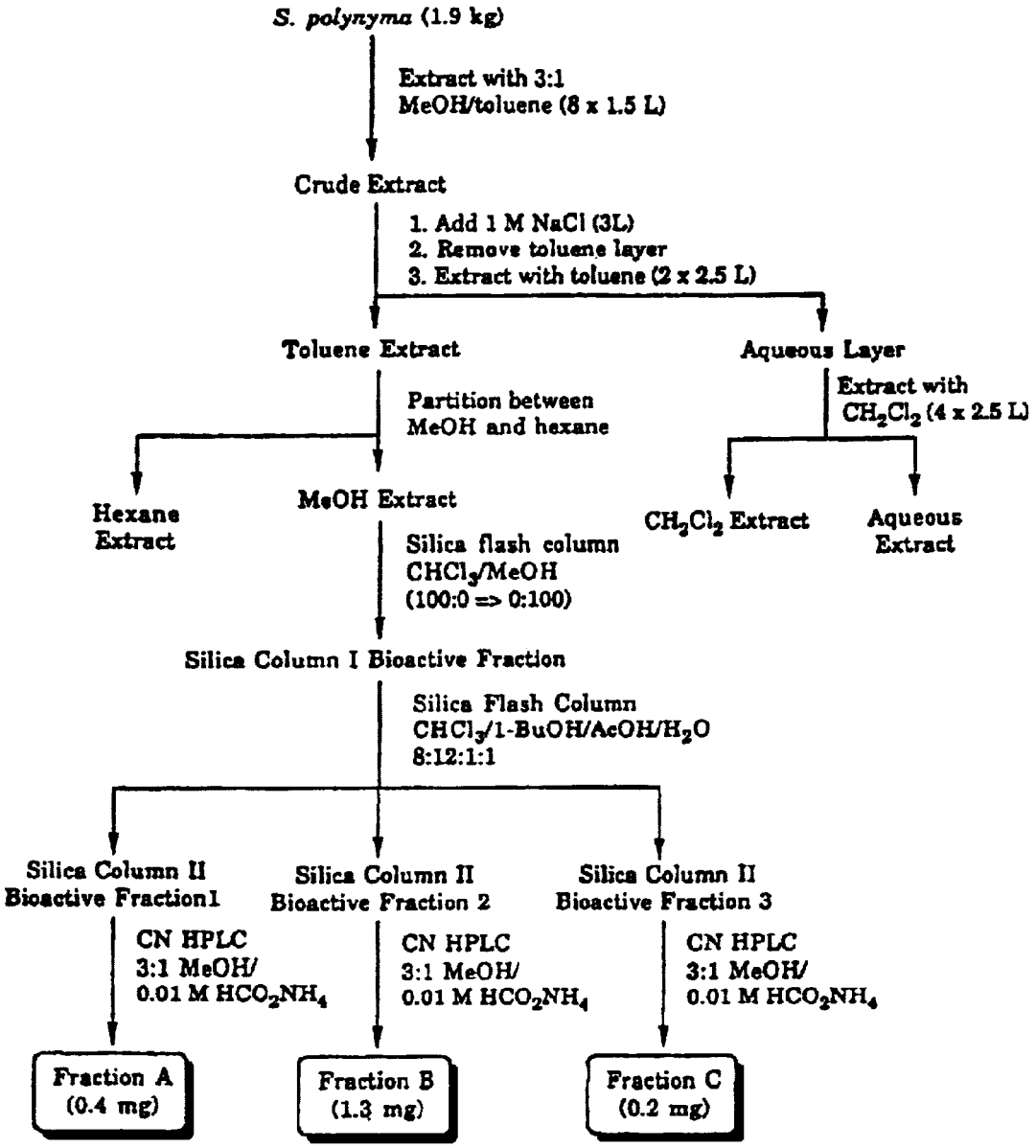
FIG. 2 illustrates the scheme used to separate the compounds described herein from extracts of the clam Spisula polynyma.

A purification scheme similar to the extraction procedure described above for the original testing of the bioactivity was employed. First 35 clams were thawed and the shells removed to give 1.9 kg (wet wt). These were allowed to stand in 3:1 methanol/toluene and filtered after several hours. This step was repeated followed by homogenization and extensive extraction with this same solvent to give a crude extract. To this was added a 1 M sodium chloride solution which caused the extract to separate into two layers. The lower aqueous layer was further extracted with toluene and the toluene layers combined. The resulting aqueous layer was then extracted with dichloromethane as shown in FIG. 2.

The toluene extract was partitioned between methanol and hexane. The cytotoxicity and cellular alteration were observed almost exclusively in the methanol fraction. The methanol extract thus obtained was applied to a silica flash column, eluting with a chloroform/methanol step gradient (100:0, 99:1, 95:5, 90:10, 85:15, 80:20, 70:30, 50:50, 0:100). The main cytotoxic and pointed-cell-forming activity eluted off the column very late, although earlier fractions did show some cytotoxicity, but no pointed cells. This late eluting was further purified by flash silica chromatography, using 8:12:1:1 chloroform/1-butanol/acetic acid/water. Fractions were neutralized with sodium bicarbonate before removing the solvent to prevent possible decomposition when they were concentrated in acid. This resulted in a series of three bioactive fractions.

It had been observed in earlier attempts at isolation that the bioactivity did not wash off of a cyano solid-phase extraction (SPE) column with methanol, but the cytotoxicity was found to elute with 3:1 methanol/0.01 M ammonium formate (0.5 mL/min). This was confirmed by chromatographing a small amount of a bioactive fraction on a cyano HPLC column with this same solvent system and then repeating the injection under the same conditions except replacing the ammonium formate solution with water. The chromatograms appeared identical except that a peak eluting at 15.6 min was only observed in the first.

The three bioactive fractions from the second silica column were each further purified by cyano HPLC with the same conditions used above (except 1 mL/min) to give three series of bioactive fractions. The ammonium formate was removed by passing the sample through a C-18 SPE column, washing first with water and then eluting with methanol. The main cytotoxicity and morphology-changing activity of each series (fractions A, B, and C) was found in a peak comparable to that discussed above. However the activity was spread throughout most of the fractions. Silica TLC (3:12:2:2 chloroform/1-butanol/acetic acid/water) indicated that fraction A (0.4 mg) contained one spot ($R_f$ 0.47), which was pink by ninhydrin. Fraction B (1.3 mg) showed this same spot as well as one slightly lower ($R_f$ 0.44, red by ninhydrin), while fraction C (0.2 mg) contained both of these and a third one ($R_f$ 0.34, purple by ninhydrin). All three showed good cytotoxicity and pointed-cell forming activity, with A exhibiting slightly more activity than B and significantly more than C. This indicated that the uppermost TLC spot must be from compound(s) which caused the morphological change in L1210 cells. These fractions were not purified further, but analyzed as mixtures. Quantitative bioassay results are discussed below.

An attempt was made to determine if a particular organ of S. polynyma contained most or all of the bioactivity. A live clam was anesthetized with diethyl ether and then dissected into nine parts: foot, digestive system, gonads, siphon, gills, heart, mantle, adductor muscles, and the remainder of the visceral mass (with foot, digestive system and gonads removed). These were identified by comparison to illustrations of other clams. Each organ was homogenized in 3:1 methanol/toluene and the resulting extract was then triturated with dichloromethane and methanol to remove salts. While all of the extracts showed cytotoxicity (Table II), only those from the gills and the gonads exhibited strong morphology-changing activity. That from the digestive system and the remainder of the visceral mass also showed weak pointed-cell forming activity, possibly due to incomplete separation from the gonads. The lack of pointed-cell-forming activity in other organs nay have resulted either from a lack of 1–3 or from a much lower concentration.

In another experiment, one foot that had been cooked for a brief period was extracted in an analogous manner. This also showed cytotoxicity, but no morphology-altering activity. However, when a larger sample of cooked material was more extensively extracted, some pointed cells were observed in the L1210 assay. Silica TLC (3:12:2:2 chloroform/1-butanol/acetic acid/water, 100 $\mu$g) of the extracts of the digestive system and gonads showed a weak ninhydrin-positive spot at $R_f$ 0.49.

Several clues to the structure of the bioactive compounds could be found in the isolation procedure. The TLC spot which correlated with the activity visualized as pink or red by ninhydrin, suggesting that the compounds contained primary amines. Also, they exhibited amphiphilic character. They were originally extracted into toluene from aqueous methanol, but they then partitioned into methanol versus hexane. While they are soluble in nonpolar solvents, they require a very polar solvent (3:12:2:2 chloroform/1-butanol/acetic acid/water) to be eluted from silica.

Only fractions A and B were reasonably pure from inactive contaminants as shown by TLC. Most of the structure determination studies were carried out on fraction B because of its size relative to the others. FIGS. 3 and 4 show the $^1$H NMR spectra of this fraction in $CDCl_3$ and $CD_3OD$, respectively. What was immediately obvious in these spectra was a peak corresponding to a long methylene chain (1.25 ppm) and several overlapping terminal methyl groups (0.87 ppm). Other peaks were not as well defined. No peaks corresponding to aromatic protons were observed, but several peaks appeared in the alkene proton region. Several others seemed to correspond to protons attached to heteroatom-substituted carbons. The major difference between the spectra in the two different solvents was that, in $CD_3OD$, a methyl doublet (1.21 ppm) downfield of the terminal methyl groups were clearly observed, while in $CDCl_3$ this resonance appeared only as an upfield shoulder on the methylene chain peak.

An authentic sample of D-trans-erythro-sphingosine (4) was obtained from Sigma for comparison with the isolated material. The $^1$H NMR spectrum thereof was similar in many respects to that of fraction B. As expected, 4 exhibited a large peak due to the long methylene chain (1.25 ppm), a terminal methyl group (0.87 ppm) and two vinyl protons (5.75 and 5.46 ppm). Of particular note was the broadness of the resonances corresponding to protons on the heteroatom-substituted carbons (4.40, 3.66, 2.85 and 2.18 ppm). Also, on silica TLC (3:12:2:2 chloroform/1-butanol/acetic acid/water), 4 had Rf 0.43 and appeared red by ninhydrin, like the lower spot in fraction B and the middle spot in C. Palmeta and Prostenik have reported that 2-amino-3-octadecanol and 4 exhibited very similar $R_f$ values (0.32 and 0.29, respectively) when eluted on paper impregnated with silicic acid with the solvent system di-isobutyl ketone/acetic acid/water (40:25:5).

Fractions A–C were also studied by several mass spectrometric methods. The largest ion in all of the spectra was m/z 286. High resolution measurement of this peak (m/z 286.3109) allowed the assignment of the molecular formula $C_{18}H_{40}NO$ ($\Delta$ 0.1 mmu) to spisulosine 285 (1). This compound derived its name, in part, from its molecular weight. This molecular formula indicated that the molecule is totally saturated. A strong peak corresponding to the loss of water from this M+H ion was observed at 268.3019 ($\Delta$ −1.5 mmu). Thus, 1 must contain a hydroxyl group. Ions corresponding to matrix adducts of m/z 286 were observed at m/z 438.3078 ($C_{22}H_{48}NO_3S_2$, $\Delta$ −0.2 mmu), 590, and 592.

One well-known primary metabolite that, like 1, consists of an 18 carbon chain substituted with hydroxyl and amine functionalities is sphingosine (4). This compound has one more oxygen and two less hydrogens than 1. The analogy appeared valid because high resolution measurement of m/z 300 for the spisulosines indicated that it was a doublet corresponding to the M+H of a higher homolog (2) of m/z 286 (300.3270, $C_{19}H_{42}NO$, $\Delta$ −0.4 mmu), together with sphingosine (4) itself (300.2914, $C_{18}H_{38}NO_2$, $\Delta$ −1.1 mmu). This also helped to explain the presence of alkene protons in the $^1$H NMR spectrum.

Several other peaks were evident in all three spectra. The ion at m/z 314 was also a doublet corresponding to $C_{20}H_{44}NO$ (314.3439, $\Delta$ −1.6 mmu), which was the molecular ion of another homolog of 1, spisulosine 313 (3), and $C_{19}H_{40}NO_2$ (314.3075, $\Delta$ −1.6 mmu) which was a homolog of sphingosine (5). Compound 4 showed matrix adducts of the M+H ion at m/z 452.2885 ($C_{22}H_{46}NO_4S_2$, $\Delta$ −1.7 mmu), 604.2831 ($C_{26}H_{54}NO_6S_4$, $\Delta$ 0.3 mmu) and 606.2995 ($C_{26}H_{56}NO_6S_4$, $\Delta$ 3.6 mmu), 5 exhibited matrix adducts of the M+H ion at m/z 464.2888 ($C_{23}H_{46}NO_4S_2$, $\Delta$ −2.0 mmu) and 618.2940 ($C_{27}H_{56}NO_6S_4$, $\Delta$ 5.1 mmu). It should be noted that, while m/z 300 and 314 were doublets of nearly equal intensity in fraction B, only one peak was measurable for the matrix adducts listed here from fraction B. This suggested that these two series of compounds, although very similar in general structure, behaved differently in FABMS. The spisulosine series (saturated) gave strong molecular ions and weaker matrix adducts, while the reverse was observed for the sphingosine series (unsaturated).

To better establish the structures identified by the data discussed above, several derivatives were prepared. The most informative was the diacetyl derivative of spisuline 285 (8). Because fraction B was the largest, a portion of it was acetylated with acetic anhydride in pyridine. This mixture of acetyl derivatives will be refered to here as AcB. By silica TLC (3:12:2:2 chloroform/1-butanol/acetic acid/water), the reaction appeared quantitative, with a new spot appearing at $R_f$ 0.86. For comparison, the triacetyl derivative of authentic 4 (9) was also synthesized by the same method.

Two series of compounds related to the spisulosines have been previously isolated. Gulavita and Scheuer reported that a Xestospongia sp. Sponge from Papua-New Guinea contained two epimeric 14-carbon amino alcohols 134 and 135. These were not isolated as the free amines, but rather the mixture was acetylated to give both the mono- (136, 137) and diacetyl compounds (138, 139) which were then separated. Jiménez and Crews have isolated several molecular ion of the underivatized 1 at m/z 286. This M+H ion (m/z 370) fragmented to give m/z 310 and 268, presumably by losing acetic acid and then the second acetyl group, respectively. The comparable ions for the other spisulosines were small, but present: m/z 384, 324 and 282 for the diacetyl derivative of 2 (144), and m/z 398, 338 and 296 for the diacetyl derivative of 3 (145). The ions from the sphingosine in the sample were too small to state definitively that they were present. This again showed that the two series of compounds had very different ionization potentials. The CIMS spectrum showed strong m/z 370 and 310 ions, but here the m/z 268 ion was very weak. The higher homologs were again seen at m/z 384 and 324 for 144, and m/z 398 and 338 for 145. Weak ions at m/z 426 and 366 were indicative of 133.

Synthesis of Spisulosine 285

To confirm the structure and determine the stereochemistry of spisulosine 285 the compound was synthesized. None of the isomers of 2-amino-3-octadecanol were previously known as natural products, but both the 2S, 3S and 2S, 3R isomers have previously been synthesized. The higher homologs are novel compounds.

A modified version of the synthesis of Prostenik and Alaupovic was used to obtain the authentic material for comparison. First, dibenzyl malonate (147) was alkylated with tetradecyl bromide (148). The resulting dibenzyl tetradecylamalonate (149) was then condensed with N-phthaloyl-L-alanyl chloride (150) to give 2-phthalimido-3-octadecanone (151) after removal of the benzyl groups and decarboxylation. This ketone was treated with excess sodium borohydride, which resulted in the reduction of one of the phthalimido carbonyls in addition to the ketone, producing both 152, which had one phthalimido carbonyl reduced to the carbinolamine, and 153, which was further reduced. These two products could be readily separated from each other by silica flash chromatography.

The reduction of 151 to 152 produced a mixture of four diastereomers because of the formation of two new chiral centers. At this point, the diastereomers were separated by cyano HPLC. The protecting group was then removed from each by further reduction with sodium borohydride followed by acetic acid.[85] As one stereocenter was removed with the protecting group, this resulted in the production of two diastereomers. Since this synthesis started with L-alanine, the two products were (2S, 3S)-2-amino-3-octadecanol (154) and (2S, 3R)-2-amino-3-octadecanol (155).

Biological Activity

While the spisulosines were quite simple compounds, as illustrated in FIGS. 1A–1F, they exhibited a very unusual type of bioactivity. As discussed above, the spisulosines caused a distinct morphological change in L1210 leukemia cells, in addition to cytotoxicity. This bioactivity, which was recorded as the percentage of living cells in which altered morphology was observed, could be observed sometimes as early as 13 h after the start of the assay and reached a maximum at 50–60 h, after which it decreased. Generally 60 cells were observed to determine this number, except in assays in which less than this number of cells remained alive. The morphological effect was usually measured 30–35 h after the start of the assay and again about 24 h later, while the cytotoxicity was determined when the number of cells in the controls reached approximately 8000, usually in 3 days after the assay was begun. It should be noted that the pointed cells were live cells and that they were counted as such for the cytotoxicity reading. Also, assays in which 100% cytotoxicity was recorded may still have contained live cells (<0.5%) which may or may not have been pointed. All morphologically-changed cells were counted in the pointed cell percentage.

This change in morphology was always observed in fractions with fairly high cytotoxicity. Generally, no significant number of pointed cells were observed in assays with less than 70% growth inhibition. However, assays in which the cytotoxicity approached 100% often had lower percentages of cells with altered morphology than those with 90–98% growth inhibition. This suggested that the altered cells might be more easily killed. It is unknown whether the cytotoxicity and the morphology change resulted from the same mechanism of action. In one instance, pointed cells from an assay were recultured and found to revert to the normal state. This suggested that the effect was reversible after the compound had been metabolized. Acetylation drastically reduces the bioactivity.

To determine if the change in morphology of L1210 cells was caused by sphingosine (4) or related compounds, several authentic compounds were obtained and assayed against L1210 cells. Both sphingosine and stearylamine (131) exhibited moderate cytotoxicity, but no morphological effect. Sphingomyelins are well-known derivatives of 4 in which a phosphoryl choline unit has been added to the primary alcohol and the amine is acylated by a fatty acid. A mixture of sphingomyelins isolated from bovine brain (Sigma), which consisted mainly of stearoyl and nervonoyl sphingomyelins (161, 162), showed minimal cytotoxicity and no pointed cells. The cytotoxicity of the phosphorylcholine derivative of 4 (163, Sigma) may be, at least, partially due to hydrolysis of 163 to 4.

Sphingosine and other long-chain amines, including stearylamine, are known to be cytotoxic. This bioactivity, as measured against Chinese hamster ovary (CHO) cells, has been shown to be maximal for 18-carbon homologs. All four stereoisomers of sphingosine were found to be almost equally active. Reduction of the double bond of 4 to produce dihydrosphingosine (164) did not affect the cytotoxicity. Addition of an N-methyl group to 164 also caused no significant change in the bioactivity, while acylation of the amine caused a large decrease in the cytotoxicity.

No cytotoxicity was reported for the related compounds (134, 135, 140–142) which have been isolated from other marine sources, however, they may not have been tested in this type of assay. A mixture of 134 and 135 was active against C. albicans (8-mm zone of inhibition for 19 $\mu$g of a mixture of the two). Xestaminol A was reported to exhibit weak activity against several Gram-positive and Gram-negative bacteria and fungi. It also showed antihelminthic activity against Nippostrongylus brasiliensis. Both 140 and 142 showed some activity against reverse transcriptase.

Possible Mode of Action

The bioactivity of the spisulosines may be due to their similarity to sphingosine. In the nomenclature of sphingolipids, spisulosine 285 would be considered 1-deoxysphinganine. The spisulosines may compete with sphingosine for binding sites or be incorporated into sphingolipids such as sphingomyelins, ceramides or gangliosides. In either case, the spisulosines could disrupt the cellular functions controlled by these compounds. Sphingosine and its derivatives are involved in the regulation of cell growth and differentiation. Sphingosine is a potent inhibitor of protein kinase C, competing with diacylglycerol for the binding site, which may explain its cytotoxicity. Structure-activity studies have shown that this inhibition requires a positively charged amine and thus N-acyl derivatives were inactive. If the spisulosines act by competing with sphingosine, this would explain the relative lack of activity of the acetylated compounds (AcB). There is growing evidence that sphingosine may act as a second messenger by regulating protein kinase C activity. It has also been shown to inhibit the differentiation of HL-60 cells treated with phorbol 12-myristate-13-acetate, a known protein kinase C activator. The spisulosines should be tested for inhibition of protein kinase C. It is unknown whether inhibition of this enzyme could cause the morphological effects observed for the spisulosines, but protein kinase C is involved in the control of cell growth and differentiation.

Experimental

NMR spectra were obtained on General Electric GN 500 and QE 300 and Varian U400 spectrometers. Samples for NMR analysis were dissolved in $CDCl_3$ or $CD_3OD$. Chemical shifts (δ) are reported in ppm downfield of tetramethylsilane (TMS) and referenced to the residual solvent peak or TMS. Low and high resolution FABMS spectra were recorded on either a VG ZAB-SE or a VG 70-SE4F spectrometer, using a 3:1 mixture of dithiothreitol-dithioerythritol (magic bullet) as the matrix. FABMS/MS spectra were recorded on a VG 70-SE4F with the same matrix, using helium as the collision gas. CI mass spectra were recorded on a VG VSE spectrometer, operating in the alternating CI/EI mode with methane as the reagent gas. IR spectra were obtained on an IBM IR/32 FTIR spectrometer. Optical rotations were measured on a JASCO DIP-370 digital polarimeter.

Chromatography

HPLC was carried out using an Alltech Econosphere cyano column (4.6×250 mm, 5 μm particle size). The HPLC system used consisted of a Beckman Model 114M pump, a Rheodyne 71 injector and either an Isco $V^4$ or Beckman 165 variable wavelength detector or a Waters 990 photodiode array detector.

Analytical thin layer chromatography (TLC) was performed on a precoated silica gel (Merck 60 F-254) and cyano bonded-phase (EM Science CN $F_{254S}$ HPTLC) plates. Spots were visualized by UV (254 nm), ninhydrin (5% in ethanol), phosphomolybdic acid (5% in ethanol) and/or iodine. Silica column chromatography was carried out on either 50–200 μm or 40–63 μm silica gel (Merck). Other column chromatography used Chromatorex ODS (Fuji-Davision 100–200 mesh) and Sephadex LH-20 (Pharmacia). High speed countercurrent chromatography (HSCCC) was performed on an Ito multi-layer coil separator-extractor (P. C., Inc.) with a #10 coil and a Milton-Roy mini-Pump. Solid phase extraction (SPE) was carried out on normal phase (silica, Alltech Maxi-Clean), reversed-phase (C-18, Waters Sep-Pak), and bonded-phase (CN, Fisher PrepSep) columns.

Biological Assays

Cytotoxicity assays against L1210 murine lymphocytic leukemia cells were performed by dissolving the samples in methanol and/or hexane were applied to the dry assay wells and the solvent was allowed to evaporate. Cells (1000) were added in minimum essential medium (MEM, 1 mL) and incubated 37° C. Inhibition of growth was recorded as the estimated percentage of living cells in sample wells versus that in control wells. This was measured when the control wells reached 8000 cells, generally three days after the start of the assay.

Morphologically-changed cells (FIGS. 1A–1F) were counted as living cells when determining the per cent inhibition of growth. Morphological changes were assessed throughout the assay period. The percentage of pointed cells was determined by counting the number of altered cells in approximately 60 living cells. This percentage varied with the length of time the assay had been running. It generally reached its maximum about 50 hours after the start of the assay, but pointed cells could be observed as early as 13 hours after the start of the assay and could usually still be seen when the per cent growth inhibition was measured. The percentages of pointed cells were often counted both after about 35 and after 55 hours. The time that this measurement was made is indicated with the data.

Antimicrobial assays were performed using the filter disk diffusion method. Paper disks (6.35 or 12.7 mm, Schleicher & Schuell) were impregnated with samples (50–500 μg) in solution and allowed to dry. These disks were then placed on agar seeded with either Bacillus subtilis, Penicellium melinii (formerly P. atrovenetum), Micrococcus luteus (formerly Sarcina lutea), Escherichia coli or Saccharomyces cerevisiae. These plates were incubated for 12–24 h (32–35° C., except P. melinii, 25–27° C.).

Extraction of S. polynyma for Initial Biological Testing

One clam (S. polynyma) was thawed and the shell removed (35.32 g, wet wt). This was placed in a blender with 350 mL of 3:1 methanol/toluene and homogenized. The yellow-brown extract was filtered and added to a 1M sodium chloride solution (100 mL). The upper toluene layer was removed and the aqueous layer extracted with toluene (75 mL). The two toluene layers were combined and the solvent was removed to give a brown oily residue (333.9 mg). The aqueous layer was further extracted with dichloromethane (2×75 mL), which gave a yellow-brown residue (18.6 mg) after removal of the solvent. The aqueous layer was then extracted with ethyl acetate (75 mL). The lower phase was the organic layer due to the presence of some dichloromethane which had remained in the aqueous phase after the last step. The upper layer was further extracted with the ethyl acetate (245 mL), the upper organic layer back-extracted with water (100 mL), and the two ethyl acetate extracts were combined to give a yellow residue (36.8 mg) after removal of the solvent. The combined aqueous layers were concentrated by one-half and extracted twice with 1-butanol (150 mL, 75 mL). The combined butanol layers were back-extracted with water (75 mL), resulting in a yellow residue (132.8 mg) after removal of the butanol. The combined aqueous layers were concentrated to give an oily light yellow residue (946.1 mg). Each extract was triturated with dichloromethane and methanol to remove salts to give the toluene (302.2 mg), dichloromethane (18.6 mg), ethyl acetate (36.7 mg), butanol (120.9 mg) and aqueous (590.4 mg) extracts which were assayed (Table I).

Fractions A, B, and C

Figure 1:
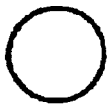
FIGS. 1A, 1B, 1C, 1D, 1E and 1F are illustrations of the cell morphologies observed in the L1210 assays of S. polynyma extracts.
Figure 1:
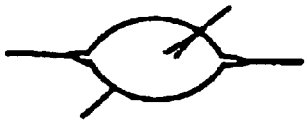
Figure 1:
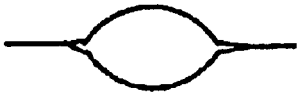
Figure 1:
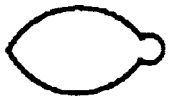
Figure 1:
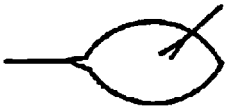
Figure 1:
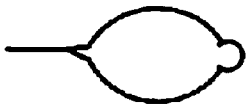

Thirty-five clams were thawed and the shells removed to give a sample of S. polynyma (1.9 kg) which was soaked in methanol/toluene (3:1, 2×1.5 L). The solids were then ground in the same solvent (6×1.5 L) and the resulting extracts filtered. A 1 M solution of sodium chloride (3 L) was added to this crude extract (12 L) and the resulting upper toluene layer removed. The aqueous layer was further extracted with toluene (2×2.5 L), followed by dichloromethane (4×2.5 L) as shown in FIG. 1.

After removal of the solvent, the toluene extract (21.55 g) was partitioned between methanol and hexane (1.5 L each). The methanol layer was further extracted with hexane (4×1 L). The combined hexane layers were concentrated to about 1.8 L and both extracts chilled (−10° C.). The two layers which resulted in each case were separated. The combined hexane layers were then extracted with methanol (0.5 L). This process resulted in a hexane and three methanol extracts of which the first methanol extract (6.8 g) contained the most bioactivity.

This bioactive methanol fraction was separated by flash silica chromatography employing a chloroform/methanol step gradient (100:0, 99:1, 95:5, 90:10, 85:15, 80:20, 70:30, 50:50, 0:100) to give 12 fractions. While the third, fourth, seventh and eighth fractions possessed some cytotoxicity, they showed no pointed-cell forming activity. This activity was found in the last two fractions along with most of the cytotoxicity.

These two fractions were combined (370 mg) and further purified by another flash silica column, using chloroform/1-butanol/acetic acid/water (8:12:1:1). To remove the acetic acid, each of the 12 fractions thus obtained was neutralized by (a) adding chloroform (one-quarter volume), (b) washing with 5% sodium bicarbonate until the pH of the aqueous layer was above 7 (2–3×half volume), and then (c) washing the organic layer with water (half volume). The third, and fourth and fifth fractions possessed all of the pointed cell-forming activity and essentially all of the cytotoxicity. Each of these fractions was separately purified by HPLC on a cyano column with 3:1 methanol/0.01 M ammonium formate (1 mL/min). Six fractions, of which the most bioactive was the fifth, were collected from each silica fraction. The ammonium formate was removed from each fraction by adding water (2–8 mL), applying the sample to an SPE column (C-18), washing with water (5–10 mL) and then eluting with methanol (5 mL). This resulted in fractions A (0.4 mg, $2\times10^{-5}$ % yield), B (1.3 mg, $7\times10^{-5}$ % yield) and C (0.2 mg, $1\times10^{-5}$ % yield), from the third, fourth and fifth silica fractions, respectively, which all eluted at $t_r$ 7.9 min.

Fraction A

White solid; silica TLC (3:12:2:2 $CHCl_3$/1-BuOH/AcOH/$H_2O$) $R_f$ 0.47 (ninhydrin-positive, pink); IR (NaCl) 2922, 2853, 1734, 1593, 1462, 1377, 1061 $cm^{-1}$ (FIG. 41); $^1H$ NMR ($CDCl_3$) δ 5.38, 5.15, 3.82, 3.67, 3.44, 3.24, 2.31, 2.03, 1.67, 1.60, 1.55, 1.25, 1.10, 0.86; FABMS m/z 606, 604, 592, 590, 466, 452, 438, 314, 300, 286, 268; CIMS m/z 354, 340, 338, 328, 326, 324, 314, 312, 310, 300, 298, 296, 286, 284, 268, 266, 149, 139, 137, 1, 123, 111, 109, 97, 95, 85, 83, 71, 69, 59, 57, 55.

Anal. Calcd. For $C_{18}H_{40}NO$: 286.3110 (M+H). Found: 286.3115 (HRFABMS).

Fraction B

White solid; silica TLC (3:12:2:2 $CHCl_3$/1-BuOH/AcOH/$H_2O$) $R_f$ 0.47 (ninhydrin-positive, pink), 0.44 (ninhydrin-positive, red); IR (NaCl) 3273, 2953, 2918, 2851, 1639, 1591, 1510, 1466, 1379, 1344, 1059, 970 $cm^{-1}$; $^1H$ NMR ($CDCl_3$) δ 5.98, 5.78, 5.55, 5.44, 5.32, 4.43, 3.78, 3.65, 3.24, 2.15, 2.08, 2.00, 1.95, 1.70, 1.44, 1.25, 1.19, 0.87; FABMS m/z 6.18.2940, 616, 606.2955, 604.2831, 592, 590, 480, 466, 464.2888, 452.2885, 438, 314.3439, 314.3075, 300.3273. 300.2914, 286, 268; CIMS m/z 354, 352, 342, 340, 338, 328, 326, 324, 314, 312, 310, 300, 298, 296, 286, 284, 282, 280, 268, 266, 219, 193, 179, 165, 149, 137, 123, 111, 109, 97, 95, 85, 83, 71, 69, 59, 57, 55.

Fraction C

White solid; silica TLC (3:12:2:2 $CHCl_3$/1-BuOH/AcOH/$H_2O$) $R_f$ 0.47 (ninhydrin-positive, pink), 0.44 (ninhydrin-positive, red), 0.34 (ninhydrin-positive, purple); IR (NaCl) 2924, 2853, 1593, 1456, 1352, 1063, 972 $cm^{-1}$; FABMS m/z 620, 618, 616, 606, 604, 602, 466, 464, 452, 438, 314, 300, 298.2741, 296, 286, 280, 268; CIMS m/z 354, 352, 340, 338, 336, 328, 326, 324, 322, 314, 312, 310, 308, 300, 298, 296, 294, 292, 286, 284, 282, 280, 278, 268, 179, 165, 149, 137, 135, 1, 123, 121, 111, 109, 97, 95, 85, 83, 81, 71, 69, 60, 59, 57, 55.

Initial Partitioning

Twenty-two S. polynyma claims were thawed and the shells removed to give 1.3 kg of the organism (wet wt). This was placed in Waring blender with 3:1 methanol/toluene (1.5 L) and ground into a thick slurry which was filtered through a layer of celite. The solid residue was further extracted (4×1.5 L) and filtered in a similar manner. The remaining solids were then placed in 5:1 methanol/toluene (750 mL) and allowed to soak for 36 h, before filtering. To the combined filtratees (7.8 L) was added 1 M sodium chloride (2 L). After removal of the upper toluene layer, the aqueous phase was extracted with toluene (2×1.5 L) and dichloromethane (3×1.5 L). The remaining aqueous phase was concentrated by one-half and extracted with ethyl acetate (2×1 L). The resulting aqueous layer was diluted with water (2 L) and extracted twice with 1-buyanol (1.5 L, 1 L). Removal of the solvents and trituration with dichloromethane and methanol resulted in the toluene (14.1 g), dichloromethane (0.75 g), ethyl acetate (1.3 g), 1-butanol (0.2 g) and aqueous (1.9 g) extracts which were assayed.

The toluene extract was partitioned between hexane and methanol (750 mL each). The resulting methanol layer was further extracted with hexane (2×750 mL, 2×500 mL). The hexane layers were combined and concentrated to about 3 L and then both extracts were chilled (−10° C.) which caused each to separate into two layers. The combined methanol layers were concentrated in vacuo to give a brown residue (methanol extract 1, 536 g). The hexane layers were further concentrated to about 1 L and back-extracted with methanol (500 mL). The solvent was removed from each of these to give the methanol extract 2 (4.26 g) and the hexane extract (4.52 g).

Fraction D

A portion of the first methanol extract (594 mg) was separated by HSCCC, using hexane/ethyl acetate/methanol/water (4:7:4:3, MP=UP) at 4 mL/min. This gave 12 fractions of which the third, fourth and fifth contained most of the bioactivity. These three fractions were combined (158 mg) and chromatographed on Sephadex LH-20, eluting with methanol. This resulted in eight fractions of which the fourth (8.4 mg) possessed the majority of the biological activity. This bioactive fraction was further purified by HPLC on a cyano column with 3:1 methanol/0.01 M ammonium formate (0.5 mL/min). Eight fractions were collected and the ammonium formate was removed from each by adding water (2–8 mL), applying the sample to an SPE column (C-18), washing with water (5–10 mL) and then eluting with methanol (5 mL). The seventh fraction ($t_r$ 15.8 min, white amorphous solid, 0.3 mg, $2\times10^{-4}$ % yield) proved to contain the bioactive compounds and is referred to here as fraction D. Silica TLC (1-BuOH/AcOH/$H_2O$, 4:1:5, upper layer) showed four spots by phoshomolybdic acid visualization: $R_f$ 0.53 (major), 0.35 (major), 0.31 (minor), and 0.19 (minor). The inactive sixth fraction showed all the same spots except Rf 0.53. The FABMS spectrum of fraction D showed intense peaks at m/z 286.3019, 300.3270 and 268.3019, and weaker peaks at m/z 314, 438, 452, 464, 590, 592, 669, 797, 809 and 825. The last three ions listed were also observed in most of the other HPLC fractions and appeared to correspond to the TLC spot at $R_f$ 0.35. Anal. Calcd. For $C_{18}H_{40}NO$: 286.3110 (M+H). Found: 286.3109 (HRFABMS).

Fraction E

A second portion of the first methanol extract described above (633 mg) was subjected to HSCCC. The solvent system employed was hexane/methanol/water (5:4:1, UP=MP, 5 mL/min), which gave poor stationary phase retention. This resulted in 10 fractions with the bioactivity spread throughout most of them. The first three fractions (310 mg) were combined and further purified by HSCCC using hexane/ethyl acetate/methanol/water (4:7:4:3, LP=MP, 2 mL/min) to give 12 fractions. The second to fifth fractions (85 mg), containing the majority of the bioactivity, were chromatographed on a C-18 flash column, eluting with a methalol/water/chloroform step gradient (90:10:0, 95:5:0, 100:0:0, 95:0:5, 90:0:10, 50:0:50). This gave 10 fractions which were all bioactive.

The fourth to sixth fractions from the first HSCCC run were combined with a side fraction from the Sephadex LH-20 column discussed under fraction D (270 mg). This material was subjected to HSCCC, using the same conditions as the second run just described except that the flow rate was 3 mL/ min. This resulted in nine fractions of which the second and third contained most of the cytotoxicity and cell-altering activity. These two fractions were combined (42 mg) and separated on a flash C-18 column, using a methanol/water step gradient (80:20, 90:10, 95:5, 100:0). This resulted in 12 fractions of which the eighth to eleventh showed morphology-altering activity and cytotoxicity. All but the first and fifth fractions from the first C-18 column were combined with the eighth to eleventh fractions from the second (50.4 mg) and separated by preparative silica TLC with chloroform/1-butanol/acetic acid/water (3:12:2:2). The plate was divided into eight fractions, which were scraped off and eluted with methanol. The residue from each fraction after removal of the solvent was triturated with dichloromethane and filtered. The fraction second from the top of the plate (Rf 0.80–0.42) contained the bioactive material and is referred to as fraction E (5.7 mg). Analytical silica TLC of fraction E, eluting with the same solvent system, showed a single spot by ninhydrin visualization ($R_f$ 0.44), but phosphomolybdic acid spray regent showed other material which streaked throughout the middle third of the plate. The FABMS spectrum of fraction B showed m/z 286 as the major peak, with lesser peaks at m/z 268, 300, 438, 452, and 592.

Fraction F

A third portion of the first methanol extract (468 mg) was separated by flash silica chromatography, using the solvent system chloroform/1-butanol/acetic acid/water (8:12:1:1). To remove the acetic acid, each of the 10 fractions thus obtained was neutralized by (a) adding water (half the volume of the fraction) and separating the two phases, (b) extracting the aqueous layer with chloroform (half volume× 2), (c) washing the combined organic layers with 5% sodium bicarbonate until the pH of the aqueous layer was above 7 (2 to 3'half volume), and then (d) washing the organic layer with water (half volume). The third fraction (24 mg), which possessed the majority of the bioactivity, was chromatographed on Sephadex LH-20, eluting with methanol, to give eight fractions. The sixth fraction (2.3 mg) was separated by repeated HPLC, using the same conditions as for the separation of fraction A–C. The ammonium formate was removed as for fraction A–C. The fraction eluting at $t_r$ 8.1 min was the most biologically active and is referred to as a fraction F. It was so small that an accurate weight could not be obtained, but probably was 100–200 $\mu$g (approx. 1 to $2\times10^{-4}$% yield). The fractions eluting later than this one also showed both cytotoxic and pointed cell-forming activity, although less potent. This suggested that either the bioactive compound(s) did not elute as a well-defined peak or that different homologs eluted at different times, but were not well separated. Silica TLC (3:12:2:2 $CHCl_3$/1-BuOH/ $AcOH/H_2O$) showed one ninhydrin-positive spot at $R_f$ 0.44. The later eluting fractions also showed this same spot, but less intense. The FABMS spectrum of fraction F shows (in decreasing order of intensity) m/z 286, 268, 300, 314, 344, 438, 452, 592, 669.

Dissection

A live clam was placed in a container with about 10 mL of diethyl ether and chilled (4° C.) for 20 h. It was dissected into nine organs: foot, digestive system (including the stomach, intestines and crystalline style sac), gonads, siphon, gills, heart, mantle, adductor muscles, and the remainder of the visceral mass. Each organ was first soaked in methanol/toluene (3:1, 10 mL/g sample) and then homogenized in a Virtis blender. The extracts were filtered and the solvent was removed. The residue was triturated with dichloromethane and methanol to give 155 mg (foot), 60 mg (digestive system), 147 mg (gonads), 101 mg (siphon) 65 mg (gills), 2.5 mg (heart), 168 mg (mantle), 101 mg (adductor muscles) and 252 mg (visceral mass).

In a separate experiment, one foot that had been cooked[a] was extracted in an analogous fashion (189 mg). A larger sample of cooked clams (483 g) was more extensively extracted by first soaking in 3:1 methanol/toluene (3×500 mL) and then homogenizing the sample in the same solvents (5×500 mL). A small sample of the combined extracts was evaporated and redissolved in methanol for assaying.

General Procedures.

Optical rotations were measured on a Jasco DIP-370 digital polarimeter, with a 3.5×50 mm 1 mL cell. Melting points were taken on a Thomas Hoover capillary melting point apparatus. $^1$H and $^{13}$C NMR were recorded on a Varian Unity-400 or Unity-500 spectrophotometer. Chemical shifts are reported in ppm relative to the solvent (7.26, $CDCl_3$ and 3.30, $CD_3OD$). High resolution (HRFAB) and fast atom bombardment (FAB) mass spectra were recorded on a VG ZAB-SE or a 70 SE4F mass spectrometer. TLC was done on Merck Silica Gel 60 Thin-Layer Plates. Chromatographic separations were done by flash chromatography using 230–400 mesh Merck silica gel. All moisture sensitive reactions were run in oven-dried glassware under an atmosphere of $N_2$. Solvents were distilled prior to use: THF from benzophenone ketyl, $CH_2Cl_2$ from $CaH_2$ other solvents used were reagent grade.

(S)-2-(N,N-Dibenzylamino)propionic acid methyl ester (30):

To a 300 mL round bottom was added 20 (10.0 g, 71.6 mmol), benzyl bromide (25.73 g, 150.4mmol), $K_2CO_3$(9.90 g, 71.6 mmol) and $CH_3CN$ (172 mL). The mixture was stirred at 60° C. until the reaction was complete by TLC. The reaction was cooler to rt and the solid was separated by filtration. The filtrate was concentrated in vacuo to give an oil which was purified by flash chromatography on silica gel (9:1 hexane/EtOAc) to give a colorless oil: $[\alpha]^{25}_D$=113.6 (c 1.2, $CHCl_3$); $^1$H NMR (400 MHz, $CDCl_3$) δ 1.35 (d, 3H, J=7.1 Hz), 3.53 (q, 1H, J=7.0 Hz), 3.65 (d, 2H, J=1.38 Hz), 3.75 (s, 3H), 3.85 (d, 2H, J=13.8 Hz), 7.22–7.42 (m, 10H); $^{13}$C NMR (100 MHz) δ 14.9, 51.1, 54.3, 56.0, 2.8, 4.1, 4.5, 139.1, 175.1; FABMS m/z 284.1 (M+H), 282.1 (M−H), 224.2 (M—$COOCH_3$); HRFABMS calcd for $C_{18}H_{22}NO_2M_r$,284.165.1 (M+H), found $M_r$ 284.1650.

(S)-2-(N,N-Dibenzylamino)-1-propanol (40):

To a suspension of $LiAlH_4$ (550 mg, 14.5 mmol) in THF (20 mL) a solution of 30 (910 mg, 3.21 mmol) in THF (2 mL) was added dropwise. The solution was stirred for 15 minutes and then heated to 65° C. for 3 hours. The reaction was cooled to 0° C. and quenched with 0.1 N HCl. The reaction was filtered through Celite and the Celite washed with THF (2×15 mL) and the solvent removed in vacuo. Flash chromatography on silica gel (4:1 hexane/EtOAc,$R_f$ =0.30) gave 750 mg (92% yield) of a colorless solid: mp 40–41° C. (from hexane) Lit. mp 40–41° C. (from hexane); $[a]^{25}_D$=+86.6 (c 1, $CHCl_3$) Lit.[6] $[\alpha]^{23}_D$=+88.2 (c 1, $CHCl_3$); $^1$H NMR (500 MHz $CDCl_3$) δ 0.98 (m, 3H), 2.98 (m, 1H), 3.13 (m, 1H), 3.35 (m, 3H), 3.45 (m, 1H), 3.81 (m, 2H), 7.19–7.41 (m. 10H); $^{13}$C NMR (1 MHz) δ 8.6, 52.9, 54.1, 62.7, 3.2, 4.5, 5.0, 5.3; FABMS m/z 256.2 (M+H), 224.2

(M—$CH_2OH$); HRFABMS calcd for $C_{17}H_{22}NO$ $M_r$ 256.1701 (M+H), found $M_r$ 256.1702. See, Stanfield et al., J. Org. Chem. 1981, 49, 4799–4800.

(S)-2-(N,N-Dibenzylamino)propionaldehyde (50):

Dry DMSO (0.53 mL, 7.43 mmol) was added to a stirred solution of oxalyl chloride (0.31 mL, 3.6 mmol) in $CH_2Cl_2$ (7.5 mL) at −78° C. The solution was allowed to stir 15 minutes followed by the addition of 40 (740 mg, 2.90 mmol) in $CH_2Cl_2$ (7.5 mL). After 30 minutes, $Et_3N$ (1.0 mL, 7.2 mmol) was added and allowed to warm to rt. The solution was extracted with satd. $NaHCO_3$ (20 mL) and the aqueous layer was extracted with $CH_2Cl_2$ (2×15 mL). The organic layer was washed with satd. NaCl solution, dried with $MgSO_4$ an concentrated in vacuo at rt to give 720 mg (98% yield) of a yellow oil which became a solid when cooled to −20° C. The aldehyde was used without further purification: mp 52–54° C. Lit. mp 55.5° C.; $[\alpha]^{26}_D$=−36.0 (c 1,$CHCl_3$ Lit. $[\alpha]^{20}_D$=−35.1 (c 1, EtOAc); $^1$H NMR (400 MHz, CDCl3) δ 1.19 (d, 2H, J=7.0 Hz), 3.34 (q, 1H, J=7.0 Hz), 3.58 (d, 2H, J=13.7 Hz), 3.74 (d, 2H, J=13.7 Hz), 7.26 (m, 2H), 7.33 (m, H), 7.42 (m,4H), 9.74 (s, 1H); $^{13}$C NMR (100 MHz) δ 6.7, 54.9, 62.8, 3.3, 4.4, 4.8, 139.1, 204.6; FABMS m/z 408.2 (M+MB), 254.2 (M+H), 22.2 (M—CHO); HRFABMS calcd for $C_{17}H_{20}NO$ $M_r$ 254.1545 (M+H), found $M_r$254.1545. See, Dix et al., Arch Pharm (Weinheim) 1995, 328, 203–205.

(2S,3R)-2-(N,N-Dibenzylamino)-3-octadecanol (60):

Mg ribbon (237 mg, 9.75 mmol), dibromoethance (16 μL, 0.189 mmol) in THF (160 μL) were added to a two neck flask fitted with a reflux condenser. A ½ mL of a 1-bromopentadecane solution (970 mg, 3.33 mmol, 3.25 mL THF) was added. After the reaction had started the remainder was added dropwise. To the grayish solution, 50 (105 mg, 0.413 mmol) in THF (0.5 mL) was added dropwise. The reaction was allowed to stir overnight followed by the addition of $H_2O$ (5 mL) and 0.1 N HCl until the solution became clear. The mixture was extracted with EtOAc (3×10 mL). The organic layer was washed with 5% $NaHCO_3$ then satd. NaCl solutions and dried with $MgSO_4$. The solvent was removed in vacuo to give an oil-solid mixture (750 mg). The crude material was purified by flash chromatography on silica (8:1 hexane/EtOAc, $R_f$ =0.34) to give 120 mg of a solid. This solid was further purified by HPLC on silica (93:7 hexane/EtOAc) to give a colorless waxy solid (94.3 mg, 49% yield): $[\alpha]^{25}_D$=+16.3 (cl, $CHCl_3$); $^1$H NMR (500 MHz, $CDCl_3$) δ 0.88 (t, 3H, J=7.0 Hz), 1.10 (d, 3H, J=6.7 Hz), 1.16–1.41 (bm, 26H), 1.56 (m, 1H), 1.69 (m, 1H), 1.79 (m 1H), 2.72 (quin, 1H, J=6.7 Hz), 3.47 (d, 2H, J=13.8 Hz), 3.60 (m, 1H), 3.76 (d, 2H, J=13.8 Hz), 7.22 (m,2H), 7.30 (m,4H), 7.34 (m,4H); $^{13}$C NMR (1 MHz) δ 8.67, 14.11, 22.68, 25.90, 29.35, 29.61, 29.64, 29.68, 29.69, 31.91, 34.27, 54.79, 57.26, 73.65, 2.89, 4.25, 4.77, 140.17; FABMS m/z 465 (M+H), 448 (M—$H_2O$), 464 (M—H), 388 (M—Ph), 224 (M—$C_{16}H_{33}O$); HRFABMS calcd for $C_{32}H_{52}NO$ $M_r$ 466.4049 (M+H), found $M_r$ 466.4037.

(2S,3R)-2-Amino-3-octadecanol (1):

To a 15 mL round bottom was added 60 (88.2 mg, 0.189 mmol) in MeOH (2 mL) and 20% Pd $(OH)_2$—C (11 mg). The mixture was stirred under 1 atm of hydrogen overnight. The catalyst was removed by filtration through a 25 mm syringe filter (0.2 μm nylon membrane) and the filter was washed with 4 mL of MeOH. The solvent was then removed in vacuo to give 51.50 mg of a white solid. The product was purified by chromatography over a 6 mL LC—Si SPE tube (90:10 $CH_2Cl_2$/MeOH followed by 100% meOH) to give 49.47 mg (92% yield) of a white solid: mp 66–67° C.; $[\alpha]^{26}_D$=+24.9 (c 1,$CHCl_3$); $^1$H NMR (500 MHz, $CD_3OD$) δ 0.89 (t, 3H, J=7.0 Hz), 1.05 (d, 3H, J=6.6 Hz), 1.20–1.56 (bm, 31H), 2.81 (qd, 1H, $J_1$=6.6 Hz, $J_2$=3.8 Hz), 3.42 (dt, 1H, $J_1$=8.8 Hz, $J_2$=3.8 Hz); $^{13}$C NMR (1 MHz) δ 14.60, 16.82, 23.90, 27.40, 30.65, 30.90, 30.95, 30.96, 33.23, 34.13, 52.33, 76.16,; FABMS m/z 286.3 (M+H), 268.3 (M—OH), HRFABMS calcd for $C_{18}H_{40}NO$ $M_r$ 286.3110 (M+H), found $M_r$ 286.3109.

A mixture of diastereomers of 3-hydroxy-2-(1-methyl-2-2-hydroxy-heptadecyl)-isoindolin-1-one (152, 22 mg) were separated by cyano HPLC with hexane/2-propanol (98:2, 1 mL/min) to give four compounds (152a–152d). The purity of each peak was determined by reinjection on HPLC. Anal. Calcd. For $C_{26}H_{44}NO_3$: 418.3321 (M+H). Found: 418.3321 HRFABMS).

152a: 4.2 mg; $t_r$ 13.3 min; $^1$H NMR ($CDCl_3$) δ 7.77 (1H, d, 7.3), 7.58 (2H, m), 7.50 (1H, m), 5.91 (2H, s), 4.51 (1H, m), 3.78 (1H,m), 1.58 (2H, m), 1.40 (3H, d, 7.1), 1.24 (26H, m), 0.87 (3H, t, 6.5); FABMS m/z 418, 400; relative ratio of diastereomers 17:1:0:0 (152a:152b:152c:152d).

152b: 13.7 mg; $t_r$ 13.9 min; $^1$H NMR ($CDCl_3$) δ 7.70 (1H, d, 7.3), 7.54 (2H, m), 7.47 (1H, m), 5.88 (2H, s), 4.37 (1H, m), 3.85 (1H, m), 1.52 (2H, m), 1.27 (3H, d, 7), 1.25 (26H, m), 0.87 (3H, t, 6.5); FABMS m/z 41, 400; relative ratio of disastereomers 1:6.8:0:0 (152a:152b:152c:152*d*).

152c: 1.4 mg; $t_r$20.0 min; $^1$H NMR ($CDCl_3$) δ 7.78 (1H, d, 7.3), 7.59 (2H, m), 7.51 (1H, m), 5.93 (2H, s), 4.12 (1H, m), 3.99 (1H, m), 1.58 (2H, m) 1.37 (3H, d, 7.0, 1.25 (26H, m), 0.87 (3H, t, 6.5); FABMS m/z 418, 400; relative ratio of diastereomers 0:2.5:45:1(152a:152b:152c:152d).

152d: 1.5 mg; $t_r$ 21.7 min; $^1$H NMR ($CDCl_3$) δ 7.77 (1H, d, 7.3), 7.59 (2H, m), 7.51 (1H, m), 5.86 (2H, s), 4.12 (1H, m), 3.90 (1H, m), 1.58 (2H, m), 1.45 (3H, d, 6.6), 1.24 (26H, m), 0.87 (3H, t, 6.5); FABMS m/z 418, 400; relative ratio of diastereomers 0:1:2:21 (152a:152b:152c:152d).

Each diasteromer was separately deprotected by the method of Osby et al.[85] Each isomer was dissolved in 2-propanol/water (6:1, 0.1 M for 152a and 152b, 0.7 M for 152c and 152d). Sodium borohydride (5–10 eq.) was added to each solution, which was then stirred at 25° C. for 24 h. Each solution was then adjusted to pH 4.5 with acetic acid and stirred at 80° C. for an additional 24 h. Ammonium formate was added to bring the pH of each solution to above 7 and then the solvent was removed from each by a stream of nitrogen. The residue from each was applied to a silica SPE column, which was first washed with hexane:2-propanol (9:1) and then the product eluted with 2-propanol. $^1$H NMR indicated that 152a and 152d produced 154 (1.15 mg, 40%, and 0.48 mg, 47% respectively), while 152b and 152c produced 155 (3.35 mg, 42%, and 0.38 mg, 40%, respectively).

154: White solid; silica TLC (3:12:2:2 $CHCl_3$/1-BuOH/AcOH/$H_2O$) $R_f$ 0.48 (ninhydrin-positive, pink); IR (NaCl) 2919, 2851, 1563, 1466, 1406, 758 $cm^{-1}$; FABMS m/z 438, 286, 268, 85, 70, 69, 57, 55, 44.

Anal. Calcd. For $C_{18}H_{40}NO$: 286.3110 (M+H). Found 286.3115 (HRFABMS).

155: White solid; silica TLC (3:12:2:2 $CHCl_3$/1-BuOH/AcOH/$H_2O$) $R_f$ 0.50 (ninhydrin-positive, pink); IR (NaCl) 3281, 2917, 2849, 1568, 1520, 1470, 1412 $cm^{-1}$; FABMS m/z 438, 286, 268, 85, 70, 69, 57, 55, 44, (FIG. 48).

Anal. Calcd. For $C_{18}H_{40}NO$: 286.3110 (M+H). Found: 286.3109 (HRFABMS).

Acetylation

A portion of fraction B (560 μg) dissolved in acetic anhydride (200 μL) and pyridine (400 μL) and was stirred at 25° C. for 4.5 h, at which time no starting material could be observed by TLC. The solvent was removed by a stream of nitrogen to give AcB: off-white solid; silica TLC $R_f$ 0.86 (3.12:2:2 $CHCl_3$/1-BuOH/AcOH/$H_2O$, phosphomolybdic acid), 0.65 (9:1 $CHCl_3$/MeOH, phosphomolybidic acid); IR (NaCl) 2922, 2853, 1741, 1651, 1547, 1460 1371, 1234, 1022, 970 $cm^{-1}$; FABMS m/z 370, 310, 268; CIMS m/z 426, 424, 412, 410, 398, 384, 370, 368, 364, 338, 324, 310, 165, 149, 139, 1, 121, 111, 97, 86, 61, 57, 55.

Anal. Calcd. For $C_{22}H_{44}NO_3$: 370.3321 (M+H). Found: 370.3326 (HRFABMS).

Triacetylsphingosine (133)

In a procedure similar to Grode and Cardellina,[93] D-erythro-sphingosine (4, 2 mg, 6.7 $\mu$mol, Sigma) in acetic anhydride (1 mL) and pyridine (2 mL) was stirred at 25° C. for 4.5 h, at which time no starting material could be observed by TLC. The solvent was removed by a stream of nitrogen to give 133: white solid; silica TLC $R_f$ 0.86 (3:12:2:2 $CHCl_3$/1-BuOH/AcOH/$H_2O$, phosphomolybdic acid), 0.65 (9:1 $CHCl_3$/MeOH, phosphomolybidic acid); FABMS m/z 580, 426, 366, 306, 264; CIMS m/z 468, 454, 426, 424, 394, 366, 364, 306, 264, 144, 85, 84, 83, 61.

(2S, 3S)-2-Acetamido-3-acetoxyoctadecane (156)

(2S, 3S)-2-amino-3-octadecanol (154, 150 $\mu$g, 0.5 $\mu$mol) in acetic anhydride (50 $\mu$l) and pyridine (100 $\mu$l) was stirred at 25° C. for 5 h, at which time no starting material could be observed by TLC. The solvent was removed by a stream of nitrogen to give 156: white solid; silica TLC $R_f$ 0.86 (3:12:2:2 $CHCl_3$/1-BuOH/AcOH/$H_20$, phosphomolybdic acid); IR (NaCl) 3286, 2924, 2853, 1740, 1653, 1541, 1456, 1371, 1238 $cm^{-1}$; FABMS m/z 522, 370, 328, 310, 286, 268. Anal. Calcd. For $C_{22}H_{44}NO_3$: 370.3321 (M+H). Found: 370.3326 (HRFABMS).

(2S, 3R)-2-Acetamido-3-acetoxyoctadecane (157)

(2S, 3R)-2-amino-3-octadecanol (155, 750 $\mu$g, 2.6 $\mu$mol) in acetic anhydride (200$\mu$L) and pyridine (400 $\mu$L) was stirred at 25° C. for 5h, at which time no starting material could be observed by TLC. The solvent was removed by a stream of nitrogen to give 157: white solid; silica TLC $R_f$ 0.86 (3:12:2:2 $CHCl_3$/1-BuOH/AcOH/$H_2O$, phosphomolybdic acid); IR (NaCl) 3289, 2917, 2849, 1728, 1637, 1545, 1464, 1369, 1240 $cm^{-1}$; FABMS m/z 522, 370, 328, 310, 286, 268.

Anal. Calcd. For $C_{22}H_{44}NO_3$: 370.3321 (M+H). Found: 370.3319 (HRFABMS).

Spisulosine 285 Acetonide (146)

A portion of fraction A (40 $\mu$g) was dissolved in acetone (200 $\mu$L) to which 0.1 N hydrochloric acid (20 $\mu$L) was added. This solution was stirred at 25° C. for 24 h, after which the solvent was removed by a stream of nitogen. FABMS indicated that a small amount of the acetonide 146 was formed: m/z 592, 452, 438, 326.3430, 300, 286, 268. Anal. Calcd. For $C_{21}H_{44}NO$: 326.3423 (M+H). Found 326.3430 (HRFABMS).

(4S, 5R)-4-Methyl-5-(n-pentadecyl)-oxazolidinone (158)

(2S, 3R)-2-amino-3-octadecanol (155, 750 $\mu$g, 2.6 $\mu$mol) was dissolved in dichloromethane (100 $\mu$L) to which 1,1'-carbonyldiimidazole (0.85 mg, 5.3 $\mu$mol) and triethylamine (0.4 $\mu$L, 2.9 $\mu$mol) was added. The solution was stirred for 5 h and then the solvent removed by a stream of nitrogen. The crude product 158 was analyzed without purification: IR (NaCl) 36, 2919, 2851, 1742, 1713, 1551, 1470, 1395, 1321, 49, 1239, 1094, 1061, 1001, 768, 743, 664 $cm^{-1}$; FABMS m/z 785, 623, 474, 406, 362, 328, 312, 286, 268.

Anal. Calcd. For $C_{19}H_{38}NO_2$: 312.2903 (M+H). Found: 312.2903 (HRFABMS).

References

The following references provide background information related to the present invention:

Faulkner, D. J. Nat. Prod. Rep. 1991, 8, 97–147.

Munro, M. H. G.; Luibrand, R. T.; Blunt, J. W. In Bioorganic Marine Chemistry;

Scheuer, P. J., Ed.; Springer-Verlag: Berlin, 1987; Vol 1, pp 93–176.

Bruening, R. C.; Oltz, E. M.; Furukawa, J.; Nakaninshi, K.; Kustin, K. J. Nat. Prod. 1986, 49, 193–204.

Pettit, G. R.; Gao, F.; Sengupta, D.; Coll, J. C.; Herald, C. L.; Doubek, D. L.; Schmidt, J. M.; Van Camp, J. R.; Rudloe, J. J.; Nieman, R. A. Tetrahedron 1991, 47, 3601–3610.

Kohmoto, S.; McConnell, O. J.; Wright, A.; Cross, S. Chem. Lett. 1987, 1687–1690.

Martin, D. G. In Countercurrent Chromatography: Theory and Practice; Mandava, N. B.; Ito, Y., Eds.; Chromatography Science 44; Dekker: New York, 1988, Chapter 9.

Marayama, W.; Kobayashi, T.; Kosuge, Y.; Yano, H.; Nunogaki, Y.; Nunogake, K. J. Chromatogr. 1982, 239, 643–649.

Schaufelberger, D. E.; Chmurny, G. N.; Beutler, J. A.; Kolek, M. P.; Alvarado, A. B.; Schaufelberger, B. W.; Muschik, G. M. J. Org. Chem. 1991, 56, 2895–2900.

Schaufelberger, D. E., Sandoz Pharma AG, personal communication, 1991.

Pettit, G. R.; Gao, F.; Herald, D. L.; Blumberg, P. M.; Lewin, N. E.; Neiman, R. A. J. Am Chem. Soc. 1991, 113, 6693–6695.

Kernan, M. R.; Molinski, T. F.; Faulkner, D. J. J. Org. Chem. 1988, 53, 5014–5020.

Murata, M.; Legrand, A. M.; Ishibashi, Y.; Fukani, M.; Yasumoto, T. J. Am. Chem. Soc. 1990, 112, 4380–4386.

Sakemi, S.; Ichiba, T.; Kohomoto, S.; Saucy, G.; Higa, T. J. Am. Chem. Soc. 1988, 110, 4851–4853.

Sakemi, S.; Higa, T.; Anthoni, U.; Christophersen, C. Tetrahedron 1987, 43, 263–268.

Sun, H. H. Cross, S. S. Gunasekera, M.; Koehn, F. E. Tetrahedron 1991, 47, 1185–1190.

Kohomoto, S.; McConnell, O. J.; Wright, A.; Koehn, F.; Thompson, W.; Lui, M.; Snader, K. M. J. Nat. Prod. 1987, 50, 336.

Ravi, B. N.; Perzanowski, H. P.; Ross, R. A.; Erdman, T. R.; Scheuer, P. J.; Finer, J.; Clardy, J. Pure & Appl. Chem. 1979, 51, 1893–1900.

Rinehart, K. L., Jr.; Sakai, R.; Stroh, J. G. U.S. Pat. No. 4,948,791, 1990; Chem. Abs. 1991, 114, 214413h.

Stierle, A. C.; Cardellina, J. H., II, Singleton, F. L. Experientia 1988, 44, 1021.

Schmitz, F. J.; Vanderah, D. J.; Hollenbeak, K. H.; Enwall, C. E. L.; Gopichand, Y.; SenGupta, P. K.; Hossain, M. B.; van der Helm, D. J. Org. Chem. 1983, 48, 3941–3945.

Dillman, R. L.; Cardellina, J. H., II J. Nat. Prod. 1991, 54, 1159–1161.

Stierle, A. C.; Cardellina, J. H., II; Strobel, G. A. Proc. Natl. Acad. Sci. USA 1988, 85, 8008–8011.

Stierle, A. A.; Cardellina, J. H., II; Singelton, F. L. Tetrahedron Lett. 1991, 32, 4847–4848.

Raub, M. F., Cardellina, J. H., II; Choudhary, M. I.; Ni, C.-Z.; Clardy, J.; Alley, M. C. J. Am. Chem. Soc. 1991, 113, 3178–3180.

Sakemi, S.; Totton, L. E.; Sun, H. H. J. Nat. Prod. 1990, 53, 995–999.

Stierle, D. B.; Faulkner, D. J. J. Nat. Prod. 1991, 54, 1134–1136.

Kohomoto, S.; McConnell, O. J.; Wright, A. Experientia 1988, 44, 85–86.

Sun, H. H., Sakemi, S. J. Org. Chem. 1991, 56, 4307–4308.
Dillman, R. L.; Cardellina, J. H., II J. Nat. Prod. 1991, 54, 1056–1061.
Sakai, R.; Kohmoto, S.; Higa, T.; Jefford, C. W.; Bernardinelli, G. Tetrahedron Lett. 1987, 28, 5493–5496.
Bobzin, S. C.; Faulkner, D. J J. Org. Chem. 1991, 56, 4403–4407.
Sakemi, S.; Sun, H. H. J. Org. Chem. 1991, 56, 4304–4307.
Keifer, P. A.; Schwartz, R. E.; Koker, M. E. S.; Hughes, R. G., Jr.; Rittschoff, D.; Rinehart, K. L. J. Org. Chem. 1991, 56, 2965–2975.
Schaufelberger, D. E.; Pettit, G. R. J. Liq. Chromatogr. 1989, 12, 1909–1917.
Pettit, G. R.; Herald, C. L.; Leet, J. E.; Gupta, R.; Schaufelberger, D. E. Bates, R. B.; Clelow, P. J.; Doubek, D. L.; Manfredi, K. P.; Rutzler, K.; Schmidt, J. M.; Tackett, L. P.; Ward, F. B.; Bruck, M.; Camou, F. Can. J. Chem. 1990, 68, 1621–1624.
Schmitz, F. J.; DeGuzman, F. S.; Choi, Y.-H.; Hossain, M. B.; Rizvi, S. K.; van der Helm, D. Pure & Appl. Chem. 1990, 62, 1393–1396.
Schmitz, F. J.; DeGuzman, F. S.; Hossain, M. B.; van der Helm, D. J. Org. Chem, 1991, 56, 804–808.
Gunawardana, G. P.; Kohmoto, S.; Gunasekera, S. P.; McConnell, O. J.; Koehn, F. E. J. Am. Chem. Soc. 1988, 110, 4856–4858.
Gunawardana, G. P.; Koehn, F. E.; Lee, A. Y.; Clardy, J.; He, H.-y.; Faulkner, D. J. J. Org. Chem. 1992, 57, 1523–1526.
Gunawardana, F. P.; Kohmoto, S.; Burres, N. S. Tetrahedron Lett. 1989, 30, 4359–4362.
Sakemi, S.; Sun, H. H.; Jefford, C. W.; Bernardinelli, G. Tetrahedron Lett. 1989, 30, 2517–2520.
Sun, H. H.; Sakemi, S.; Burres, N.; McCarthy, P. J. Org. Chem. 1990, 55, 4964–4966.
Perry, N. B.; Blunt, J. W.; Munro, M. H. G.; Higa, T.; Sakai, R. J. Org. Chem. 1988, 53, 43–44.
Jares-Erijman, E. A.; Sakai, R.; Rinehart, K. L. J. Org. Chem. 1991, 56, 5712–5715.
Berlinck, R. G. S.; Braekman, J. C.; Daloze, D.; Hallenga, K; Ottinger, R.; Bruno, I.; Riccio, R. Tetrahedron Lett. 1990, 31, 6531–6534.
Kashman, Y.; Hirsh, S.; McConnell, O. J.; Ohtani, I.; Kusumi, T.; Kakisawa, H. J. Am. Chem. Soc. 1989, 111, 8925–8926.
Rinehart, K. L.; Holt, T. G.; Fregeau, N. L. Stroh, J. G.; Keifer, P. A.; Sun, F.; Li, L. H.; Martin, D. G. J. Org. Chem. 1990, 55, 4512–4515.
Wright, A. E.; Forleo, D. A.; Gunawardana, G. P.; Gunasekera, S. P.; Koehn, F. E.; McConnell, O. J. J. Org. Chem. 1990, 55, 4508–4512.
Vaught, K. C. A. Classification of the Living Mollusca; Abbott, R. T.; Boss, K. J., Eds.; American Malacologists: Melbourne, Fla. 1989; pp 113–6.
Brusca, R. C.; Brusca, G. J. Invertebrates; Sinauer Associates: Sunderland, Mass., 1990; pp 706–709.
Barnes, R. D. Invertebrate Zoology; 4th ed.; Saunders College: Philadelphia, 1980; p 425.
Engemann, J. G.; Hegner, R. W. Invertebrate Zoology; 3rd ed.; Macmillan: New York, 1981; pp 454–467.
Palameta, B.; Prostenik, :M. Croat. Chem. Acta 1961, 33, 133–135.
Kawano, Y.; Highchi, R.; Isobe, R.; Komori, T. Liebigs Ann. Chem. 1988, 19–24.
Gulavita, N. K.; Scheuer, P. J. J. Org. Chem. 1989, 54, 366–369.
Jimenez, C.; Crews, P. J. Nat. Prod. 1990, 53, 978–982.
Mori, K.; Matsuda, H. Liebigs Ann. Chem. 1992, 131–137.
Prostenik, M.; Alaupovie, P. Croat. Chem. Acta 1957, 29, 393–402.
Osby, J. O.; Martin, M. G.; Ganem, B. Tetrahedon Lett. 1984, 25, 2093–2096.
Stoffel, W. Ann. Rev. Biochem. 1971, 40, 57–82.
Merrill, A. H., Jr.; Nimkar, S.; Menaldino, D.; Hannun, Y. A.; Loomis, C.; Bell, R. M., Tyagi, S. R.; Lambeth, J. D.; Stevens, V. L.; Hunter, R.; Liotta, D. C. Biochemistry 1989, 28, 3138–3145.
Hannun, Y. A.; Bell, R. B. Scince 1989, 243, 500–507.
Merrill, A. H., Jr. J. Bioenerg. Biomem. 1991, 23, 83–104.
Witten, J. L.; Schaffer, M. H.; O'Shea, M.; Cook, J. C.; Hemling, M. E.; Rinehart, K. L., Jr. Biochem. Biophys. Res. Commun. 1984, 124, 350–358.
Shaw, P. D.; McClure, W. D.; Van Blaricom, F.; Sims, J.; Fenical, W.; Rude, J. In Food and Drugs from the Sea 1974; Webber, H. H.; Ruggieri, G. D., Eds.; Marine Technological Society: Washington, D.C., 1976; pp 429–433.
Herrmann, E. C., Jr. Progr. Med. Virol. 1961, 3, 158–192.
Grode, S. H.; Cardellina, J. H., II Lipids, 1983, 18, 889–893.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

[1. A synthetic method for the formation of spisulosine compounds comprising the steps of:

protecting the α-amino group of a compound having the formula 20:

20

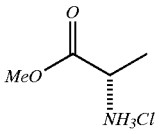

to form a compound of formula 30:

30

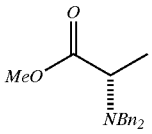

reducing the compound of formula 30 to provide a compound of formula 40:

40

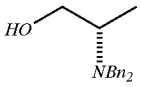

oxidizing the compound of formula 40 to provide a compound of formula 50:

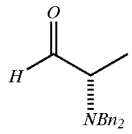

reacting the compound of formula 50 with Grignard reagent having the formula $CH_3(CH_2)_nMgBr$ to form a compound having the formula 60:

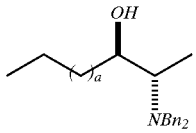

wherein n=14, 15 or 16; and deprotecting the amino group in compound 60 by catalytic hydrogenation to afford a spisulosine compound.]

[2. The process of claim 1, wherein n is 14 and the spisulosine compound generated is Spisulosine 285.]

[3. The process of claim 1, wherein n is 15 and the spisulosine compound generated is Spisulosine 299.]

[4. The process of claim 1, wherein n is 16 and the spisulosine compound generated is Spisulosine 313.]

*5. A synthetic method for the formation of spisulosine compounds comprising the steps of:*

*protecting the α-amino group of a compound having the formula 20:*

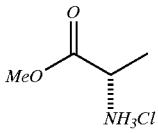

*to form a compound of formula 30:*

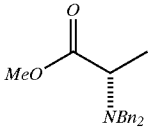

*reducing the compound of formula 30 to provide a compound of formula 40:*

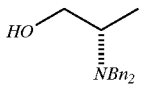

*oxidizing the compound of formula 40 to provide a compound of formula 50:*

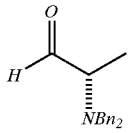

*reacting the compound of formula 50 with Grignard reagent having the formula $CH_3(CH_2)_nMgBr$ to form a compound having the formula 60:*

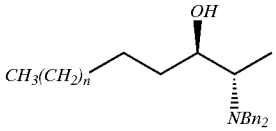

*wherein n=12, 13 or 14; and*

*deprotecting the amino group in compound 60 by catalytic hydrogenation to afford a spisulosine compound.*

*6. The process of claim 5, wherein n is 12 and the spisulosine compound generated is Spisulosine 285.*

*7. The process of claim 5, wherein n is 13 and the spisulosine compound generated is Spisulosine 299.*

*8. The process of claim 5, wherein n is 14 and the spisulosine compound generated is Spisulosine 313.*

*9. A synthetic method for the formation of spisulosine compounds comprising the steps of:*

*oxidizing a compound of formula 40:*

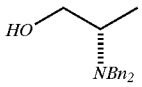

*to provide a compound of formula 50:*

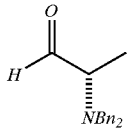

*reacting the compound of formula 50 with Grignard reagent having the formula $CH_3(CH_2)_nMgBr$ to form a compound having the formula 60:*

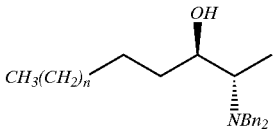

*wherein n=12, 13, or 14; and*

*deprotecting the amino group in compound 60 by catalytic hydrogenation to afford a spisulosine compound.*

*10. The process of claim 9, wherein n is 12 and the spisulosine compound generated is Spisulosine 285.*

*11. The process of claim 9, wherein n is 13 and the spisulosine compound generated is Spisulosine 299.*

*12. The process of claim 9, wherein n is 14 and the spisulosine compound generated is Spisulosine 313.*

* * * * *